United States Patent
Barrow et al.

(10) Patent No.: US 12,097,184 B2
(45) Date of Patent: *Sep. 24, 2024

(54) FORMULATIONS OF PSILOCIN THAT HAVE ENHANCED STABILITY

(71) Applicant: Mind Medicine, Inc., New York, NY (US)

(72) Inventors: Robert Barrow, Madison, WI (US); Peter Mack, Chapel Hill, NC (US); Stephen Schneider, Raleigh, NC (US); Jon Schroeder, Madison, WI (US); Gerald S. Jones, Norwood, MA (US)

(73) Assignee: Mind Medicine, Inc., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 18/326,480

(22) Filed: May 31, 2023

(65) Prior Publication Data
US 2023/0285359 A1  Sep. 14, 2023

Related U.S. Application Data

(63) Continuation of application No. 17/883,509, filed on Aug. 8, 2022, which is a continuation-in-part of application No. 17/687,568, filed on Mar. 4, 2022.

(60) Provisional application No. 63/184,691, filed on May 5, 2021, provisional application No. 63/157,682, filed on Mar. 6, 2021.

(51) Int. Cl.
*A61K 31/4045* (2006.01)

(52) U.S. Cl.
CPC .................. *A61K 31/4045* (2013.01)

(58) Field of Classification Search
CPC .................................................. A61K 31/4045
See application file for complete search history.

(56) References Cited

U.S. PATENT DOCUMENTS

| | | | |
|---|---|---|---|
| 11,000,534 B1 | 5/2021 | Sippy | |
| 11,298,388 B2 | 4/2022 | Lightburn et al. | |
| 11,312,684 B1 * | 4/2022 | Nichols | C07C 63/08 |
| 11,324,762 B2 | 5/2022 | Sippy | |
| 11,331,357 B2 | 5/2022 | Lightburn et al. | |
| 11,591,353 B2 * | 2/2023 | Slassi | A61K 31/675 |
| 2018/0021326 A1 * | 1/2018 | Stamets | A61K 31/4045 424/195.15 |
| 2021/0015833 A1 | 1/2021 | LaRosa et al. | |
| 2021/0393717 A1 | 12/2021 | Lightburn et al. | |
| 2022/0054402 A1 | 2/2022 | Kaufman | |
| 2022/0152136 A1 | 5/2022 | Lightburn et al. | |

FOREIGN PATENT DOCUMENTS

| | | | | |
|---|---|---|---|---|
| WO | WO-2020157569 A1 * | 8/2020 | | A61K 31/05 |
| WO | 20210811138 | 4/2021 | | |
| WO | WO-2021188812 A1 * | 9/2021 | | A61K 31/01 |
| WO | 2021253116 | 12/2021 | | |
| WO | 2022082320 | 4/2022 | | |

OTHER PUBLICATIONS

Saal, C. et al., Pharmaceutical salts: A summary on doses of salt formers from the Orange Book, Jun. 5, 2013, European Journal of Pharmaceutical Sciences, vol. 49, 614-623 (Year: 2013).*
Pubchem, "Benzenesulfonate", https://pubchem.ncbi.nlm.nih.gov/compound/91526, accessed May 9, 2024 (Year: 2024).*
Mitchell, M.J., Billingsley, M.M., Haley, R.M. et al. Engineering precision nanoparticles for drug delivery. Nat Rev Drug Discov 20, 101-124 (2021). https://doi.org/10.1038.s41573-020-0090-8 (Published Dec. 4, 2020).†
U.S. Appl. No. 63/148,052, US, filed Apr. 26, 2022, Charles D. Nichols.†
Ita KB, Du Preez J, Lane ME, Hadgraft J, du Plessis J. Dermal delivery of selected hydrophilic drugs from elastic liposomes: effect of phospholipid formulation and surfactants. J Pharm Pharmacol. Sep. 2007;59(9):1215-22. doi: 10.1211/jpp.59.9.0005. PMID: 17883892. (Published 2007).†

* cited by examiner
† cited by third party

*Primary Examiner* — Bethany P Barham
*Assistant Examiner* — Paul Hoerner
(74) *Attorney, Agent, or Firm* — Kohn & Associates PLLC; Kenneth I. Kohn; Laura S. Dellal

(57) ABSTRACT

A composition of psilocin that is stable including at least one agent or chemical modification that provides enhanced stability. A method making stable psilocin, by providing a formulation of psilocin including at least one agent or chemical modification that provides enhanced stability. A method of treatment of a disease or condition, by administering a composition of psilocin that is stable to an individual and treating the disease or condition.

2 Claims, 48 Drawing Sheets

FIGURE 1A

| Compound Name | Group | Dosage (mg/kg) | Dose Volume (mL/kg) | Weighed Amount (mg) | Dosing Solution Conc. (mg/mL) | Vehicle (mL) | Vehicle | Appearance |
|---|---|---|---|---|---|---|---|---|
| Psilocin | 1 | 5 | 5 | 10.3 | 1.00 | 10.30 | PBS | clear solution |
| Psilocybin | 2 | 5 | 5 | 10.63 | 1.00 | 10.63 | PBS | clear solution |
| Psilocin | 3 | 5 | 10 | 10 | 0.50 | 20.00 | PBS | clear solution |
| Psilocybin | 4 | 5 | 10 | 11.38 | 0.50 | 22.76 | PBS | clear solution |

Test System
Species/Strain: Male/Female SD Rat
No. of Animals Dosed: 24

FIGURE 1B

| Group | # Animals/Sex | Test Article | Route of admin. | Dosage (mg/kg) | Dose (mg/mL) | Dose (mL/kg) | Sample Collection Time Points |
|---|---|---|---|---|---|---|---|
| 1 | 3/M 3/F | Psilocin | IV* | 5 | 1 | 5 | 3min, 7min, 15min, 30min, 1h, 2h, 4h, 8h and 24h |
| 2 | 3/M 3/F | Psilocybin | IV* | 5 | 1 | 5 | 3min, 7min, 15min, 30min, 1h, 2h, 4h, 8h and 24h |
| 3 | 3/M 3/F | Psilocin | PO | 5 | 0.5 | 10 | 10min, 20 min, 40 min, 1h, 2h, 4h, 6h, 8h and 24h |
| 4 | 3/M 3/F | Psilocybin | PO | 5 | 0.5 | 10 | 10min, 20 min, 40 min, 1h, 2h, 4h, 6h, 8h and 24h |

* Administered the IV dose via femoral cannula

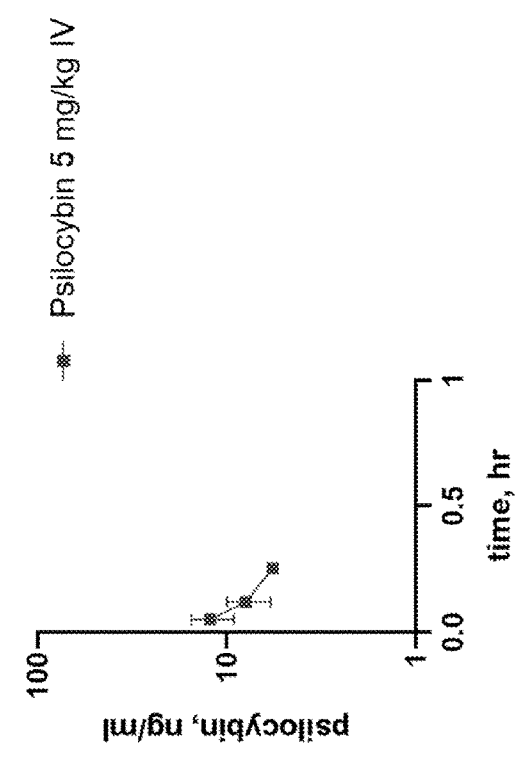
FIGURE 2A
FIGURE 2B
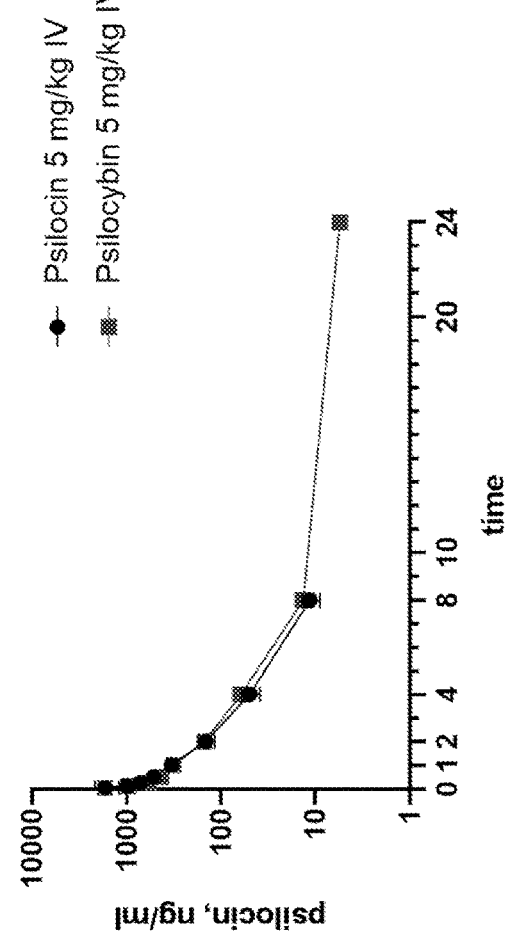
FIGURE 2C
| Group | No pts used for $t_{1/2}$ | $t_{1/2}$ (h) | $C_{max}$ (ng/mL) | $AUC_{last}$ (h*ng/mL) | $AUC_{Inf}$ (h*ng/mL) | $AUC_{Extr}$ (%) | $V_z$ (L/kg) | $V_{ss}$ (L/kg) | CL (mL/min/kg) | MRT (h) |
|---|---|---|---|---|---|---|---|---|---|---|
| Psilocin IV | 3 | 1.66 | 1694.568 | 1242 | 1269 | 2.1 | 9.41 | 5.90 | 65.68 | 1.30 |
| Psilocybin IV | 7 | 3.72 | 1722.738 | 1367 | 1397 | 2.1 | 19.21 | 11.64 | 59.67 | 2.69 |

| Group | No pts used for $t_{1/2}$ | $t_{1/2}$ (h) | $t_{max}$ (h) | $C_{max}$ (ng/mL) | $AUC_{last}$ (h*ng/mL) | $AUC_{Inf}$ (h*ng/mL) | $AUC_{Extr}$ (%) | MRT (h) | F (%) |
|---|---|---|---|---|---|---|---|---|---|
| Psilocin PO | 3 | 7.62 | 0.67 | 152.757 | 998 | 1082 | 7.8 | 5.49 | 80.4 |
| Psilocybin PO | 3 | 6.83 | 1.00 | 313.791 | 1122 | 1171 | 4.2 | 4.26 | 82.1 |

Figure 5

| Compound Name | Group | Vehicle | Nominal (mg/mL) | Measured (mg/mL) | Relative Error (%) |
|---|---|---|---|---|---|
| Psilocin Free Base** | 1 | PBS | 1.00 | 0.710 | -29.0 |
| | | | | 0.690 | -31.0 |
| Psilocybin | 2 | PBS | 1.00 | 0.869 | -13.1 |
| | | | | 0.887 | -11.3 |
| Psilocin Free Base*/** | 3 | PBS | 0.50 | 0.134 | -73.3 |
| | | | | 0.128 | -74.4 |
| Psilocybin | 4 | PBS | 0.50 | 0.461 | -7.7 |
| | | | | 0.433 | -13.5 |

*The presented concentration was confirmed by reassay.
**The color of the solution is getting darker over time. Part of the compound may have decomposed during the storage and freeze-thaw cycles.

1H, Psilocin tartrate in DMSO-d6

1H, Psilocin tartrate in DMSO-d6

1H, Psilocin tartrate in DMSO-d6

1H, Psilocin tartrate in DMSO-d6

FIGURE 20

Degree of Degradation Relative to Positive Control

| Stress Condition | Duration | Estimated Degradation (%) |
|---|---|---|
| Acid Hydrolysis (1N HCl) | 2 Hours | 0.00% |
| | 6 Hours | 0.874% |
| | 24 Hours | 0.413% |
| Base Hydrolysis (1N NaOH) | 2 Hours | 60.2% |
| | 6 Hours | 99.6% |
| | 24 Hours | 100% |
| Oxidative Stress ($H_2O_2$) | 2 Hours | 100% |
| | 6 Hours | 100% |
| | 24 Hours | 100% |
| Elevated Temperature (Solution) 40°C | 1 Day | 0.139% |
| | 3 Days | 4.30% |
| | 5 Days | 9.79% |
| Elevated Temperature (Solid) 60°C | 1 Day | 2.46% |
| | 3 Days | 4.07% |
| | 5 Days | 9.00% |
| UV Radiation (Solution) 254 nm | 1.75 Hours | 8.98% |

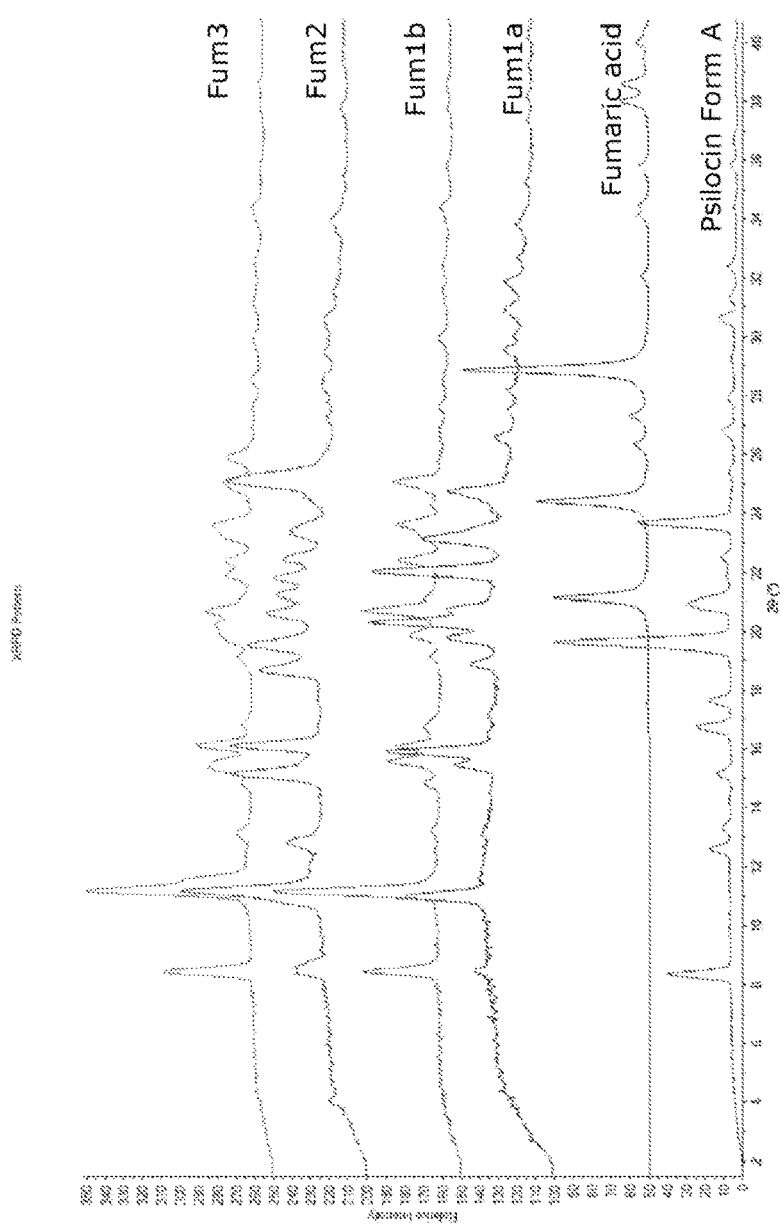

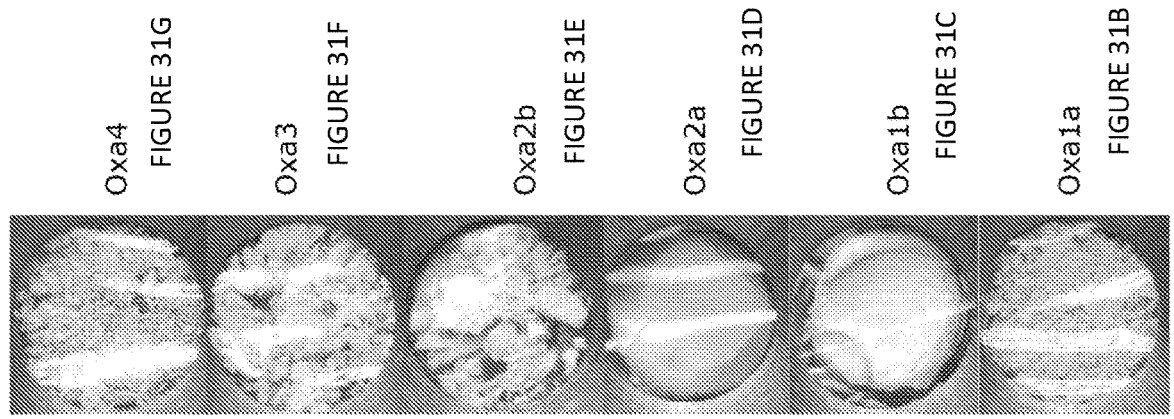
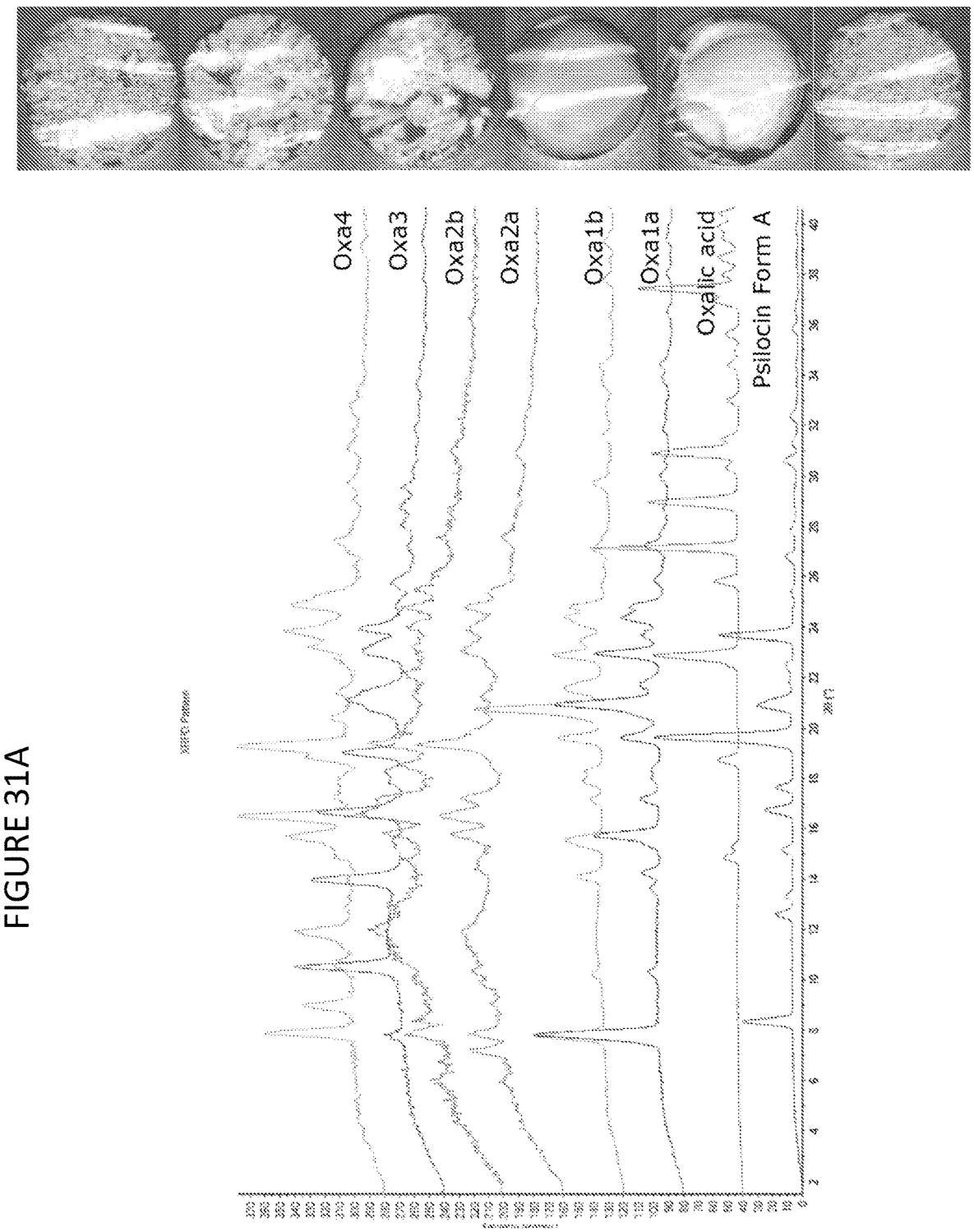
FIGURE 31A

FIGURE 33A
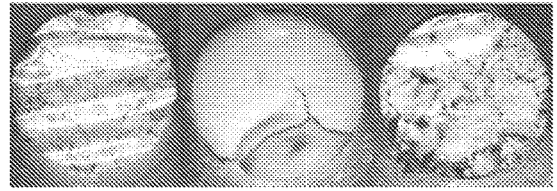
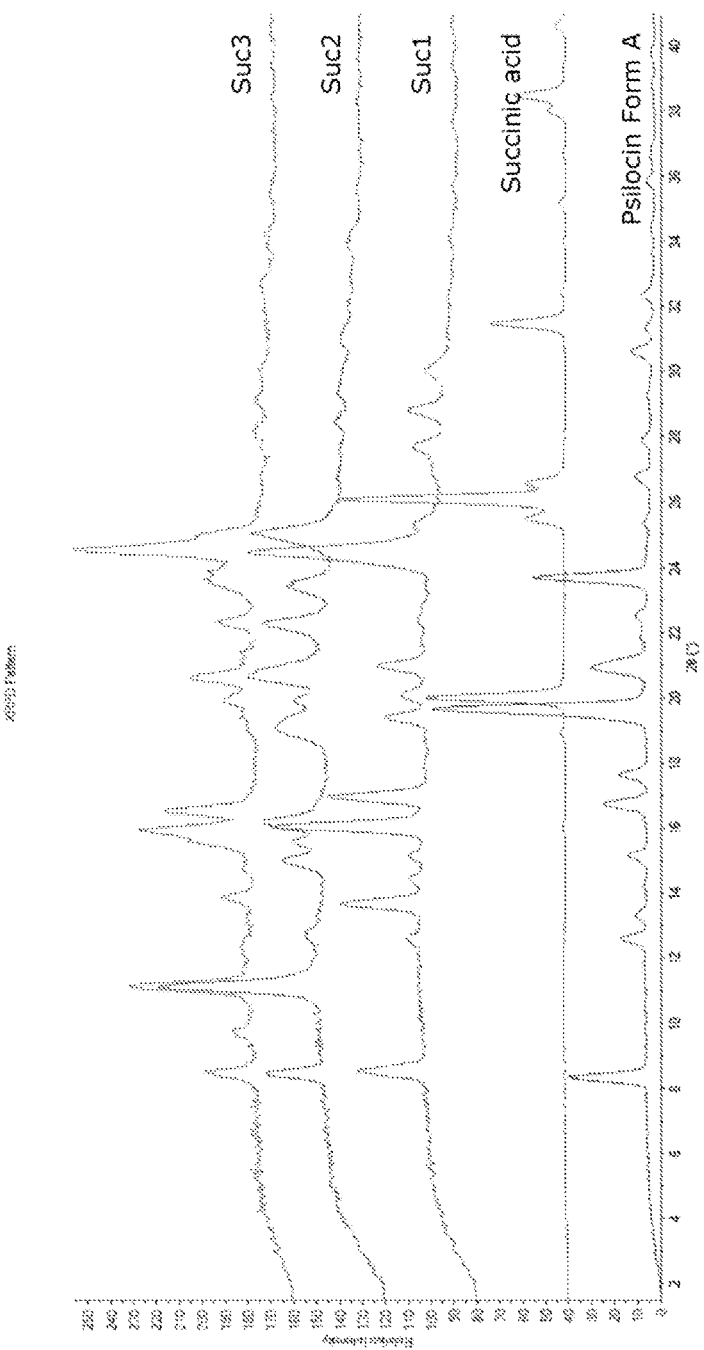

FORMULATIONS OF PSILOCIN THAT HAVE ENHANCED STABILITY

BACKGROUND OF THE INVENTION

1. Technical Field

The present invention relates to compositions of psilocin and methods for providing stable compositions of psilocin as well as therapeutic indications.

2. Background Art

Psilocybin (4-phosphoryloxy-N, N-dimethyltryptamine) is a psychedelic substance found in several species of psychedelic mushrooms (Psilocybe) which cause "mind-altering" effects in humans (Hofmann et al., 1959; Nichols, 2004). Isolated in 1958 by A. Hofmann, psilocybin is a prodrug that must undergo biotransformation to the active drug psilocin. Psilocin's psychoactive effects are predominately mediated via 5-HT2A receptors (Rickli et al., 2016; Vollenweider et al., 1998). Recently, psilocybin has been repurposed and investigated for the treatment of cluster headache, obsessive compulsive disorder, anxiety and depression, and in alcohol use disorder (Bogenschutz et al., 2018; Carhart-Harris et al., 2017; Griffiths et al., 2016; Grob et al., 2011; Johnson et al., 2017; Moreno et al., 2006; Ross et al., 2016; Sewell et al., 2006).

Psilocybin is both difficult and costly to manufacture. Shirota, et al. describe producing psilocybin from 4-hydroxyindole, which costs over $200 per gram as a starting substrate. Due to this difficulty, which is largely driven by the final manufacturing step to convert psilocin to psilocybin, scalability of the synthetic process to commercial scale is also uncertain. Other groups in Denmark have tried making psilocybin with yeast, however, while their methods eliminate the need for 4-hydroxyindole, their product yield is poor because they generate large amounts of psilocin (4-hydroxy-N,N-dimethyltryptamine), the metabolite of psilocybin.

Psilocybin is a prodrug that requires biotransformation to psilocin mediated by alkaline phosphatases in order to have pharmacological activity. Psilocybin is both not permeable in intestinal epithelia (Eivindvik and Rasmussen, 1989) or CNS. Psilocin itself is not used in medical treatment because it is known to have poor stability due to photodegradation and oxidation in both ambient (i.e., exposed to air) and aqueous environments. Lenz, et al. (Angew. Chem. Int. Ed. 2020, 59, 1450-1454) report that upon injury, psychotropic psilocybin-producing mushrooms instantly develop an intense blue color and two enzymes from *Psilocybe cubensis* carry out a two-step cascade to prepare psilocybin for oxidative oligomerization that leads to blue products. The phosphatase PsiP removes the 4-O-phosphate group to yield psilocin, while PsiL oxidizes its 4-hydroxy group. The PsiL reaction was monitored by in situ 13C NMR spectroscopy, which indicated that oxidative coupling of psilocyl residues occurs primarily via C-5. MS and IR spectroscopy indicated the formation of a heterogeneous mixture of preferentially psilocyl 3- to 13-mers and suggest multiple oligomerization routes, depending on oxidative power and substrate concentration.

Anastos 2006 describe improvements in psilocin sample stability when protected from light, however, there is still a 50% peak loss over 14 days which is not considered stable and is not viable for a pharmaceutical composition or drug product. Psilocin in biological samples (such as blood or urine) is also unstable and is degraded by both non-enzymatic and enzymatic processes (Lindenblatt 1998; Hasler 1997; Martin 2012). Improvements in psilocin stability in biological samples have been achieved by addition of 25 mM ascorbic acid, though greater than 5% of psilocin can still be lost in these samples suggesting this procedure is not sufficient to stabilize psilocin (Brown 2017; Hasler 1997). Others have tried to find other stable versions of psilocin, such as by synthesizing psilocin glucuronide which provides a greater long-term stability after six months in in deep frozen serum and urine samples than psilocin, and a short-term stability for one week in whole blood at room temperature and in deep frozen samples better than that of psilocin (Martin et al., 2014). Psilocin glucuronide is not suitable as a drug formulation as it is unlikely to be able to permeate the blood-brain barrier and is likely to be rapidly eliminated in urine.

As a result of the required biotransformation of psilocybin to psilocin, the pharmacokinetics of psilocin are highly variable following administration of psilocybin by multiple routes of administration. In fact, even following intravenous administration of psilocybin, maximum plasma concentrations of psilocin can vary over three-fold between individuals, resulting in an increased risk of adverse effects or inability to achieve efficacious concentrations (Hasler et al., 1997).

Others have sought to stabilize psilocin in biological samples (i.e., plasma, urine) to enhance the stability of these samples prior to analysis through the addition of ascorbic acid, freeze drying and use of ultracold storage conditions (Brown et al., 2017; Hasler et al., 1997; Martin et al., 2012); however, these attempts were only partially successful at stabilizing psilocin in biological samples with psilocin continuing to demonstrate significant instability in biological samples. No prior art exists disclosing an attempt to stabilize psilocin in a pharmaceutical formulation for administration to humans or other animals.

There remains a need for methods of increasing the stability of psilocin and using psilocin in treatments as a more efficacious, cost effective, and robust therapeutic, especially for neurological, psychological, substance use and pain disorders.

SUMMARY OF THE INVENTION

The present invention provides for a composition of psilocin that is stable including at least one agent or chemical modification that provides enhanced stability.

The present invention provides for a method making stable psilocin, by providing a formulation of psilocin including at least one agent or chemical modification that provides enhanced stability.

The present invention provides for a method of treatment of a disease or condition, by administering a composition of psilocin that is stable to an individual and treating the disease or condition.

DESCRIPTION OF THE DRAWINGS

Other advantages of the present invention are readily appreciated as the same becomes better understood by reference to the following detailed description when considered in connection with the accompanying drawings wherein:

FIG. 1A is a table showing a study design, and FIG. 1B is a table showing a study design;

FIG. 2A is a graph showing plasma psilocin after IV dose, FIG. 2B is a graph showing plasma psilocybin after IV dose, and FIG. 2C is a table showing values of PK characteristics;

FIG. 5 is a table showing results of the analysis of dosing solutions;

FIG. 20 is a chart showing degree of degradation of psilocin free base compared to a control;

FIG. 27A is a graph of XRPD patterns of fumarate salts (Fum1a, Fum1b, Fum2, and Fum3), FIG. 27B is a photograph showing vacuum dried fumarate salt Fum1a, FIG. 27C is a photograph showing vacuum dried fumarate salt Fum1b, FIG. 27D is a photograph showing wet fumarate salt Fum2, and FIG. 27E is a photograph showing wet fumarate salt Fum3;

FIG. 31A is a graph of XRPD patterns of oxalate salts (Oxa 1a to Oxa4), FIG. 31B is a photograph showing vacuum dried oxalate salt Oxa1a, FIG. 31C is a photograph showing wet oxalate salt Oxa1b, FIG. 31D is a photograph showing wet oxalate salt Oxa2a, FIG. 31E is a photograph showing vacuum dried oxalate salt Oxa2b, FIG. 31F is a photograph showing vacuum dried oxalate salt Oxa3, and FIG. 31G is a photograph showing vacuum dried oxalate salt Oxa4;

FIG. 33A is a graph of XPRD patterns of succinate salts (Suc1 to Suc3), FIG. 33B is a photograph showing the vacuum dried succinate salt Suc1, FIG. 33C is a photograph showing the wet succinate salt Suc2, and FIG. 33D is a photograph showing the vacuum dried succinate salt Suc3;

DETAILED DESCRIPTION OF THE INVENTION

Figures 3A, 3B:
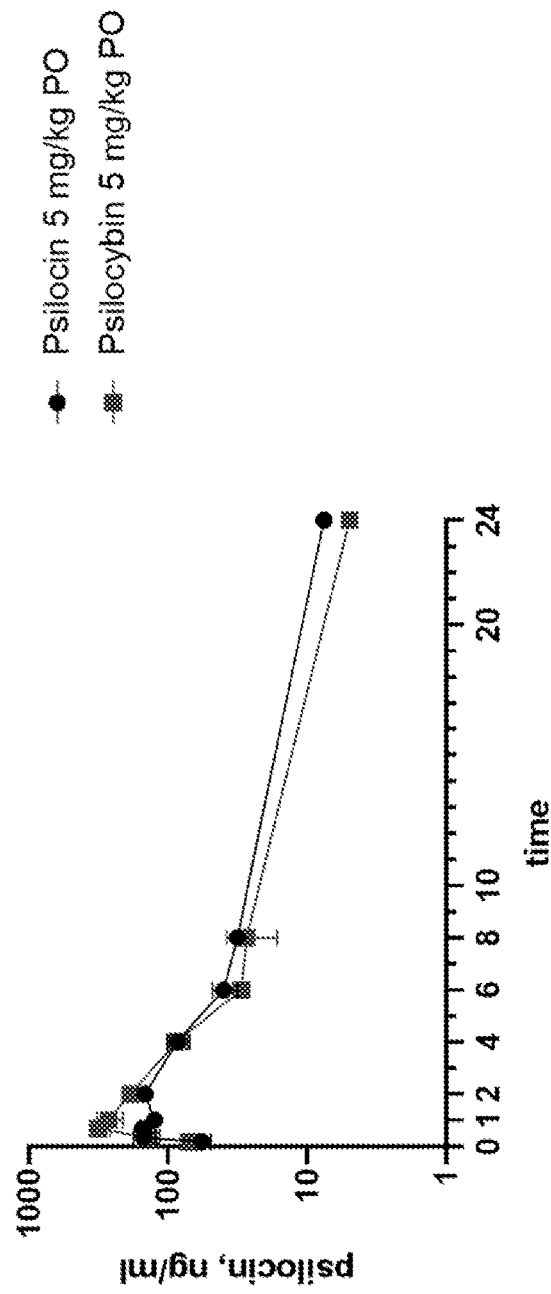
FIG. 3A is a graph showing plasma psilocin after PO dose.
FIG. 3B is a chart showing values of PK characteristics.

The present invention provides for compositions of psilocin that are stable by various mechanisms. These compositions enable the administration of the active drug psilocin, which does not require biotransformation to be active, instead of the prodrug (psilocybin) that does not have pharmacological activity in vivo and does require biotransformation into psilocin to provide its effects. Use of psilocin instead of psilocybin can provide reduced inter-subject variability in exposure to the active molecule psilocin (Hasler 1997 shows that even after IV administration of psilocybin, inter-individual variability of psilocin concentrations was over 3-fold, whereas direct psilocin administration does not result in such variability, likely due to alkaline phosphatase metabolism and glucuronidation as well as other mechanisms). Ultimately, these advantages of psilocin result in enhanced efficacy and reduced risk of side effects compared to use of psilocybin.

"Stable" as used herein, can refer to shelf-stable (i.e., stable at ambient room temperature and humidity), as well as stable in cold storage or storage under inert conditions. For example, shelf-life stability can be 3 months, 6 months, 1 year, or longer.

The composition can include at least one agent that provides enhanced stability such as a photostabilizing agent or an antioxidant. Combinations of these agents can also be used (Anastos 2006 states that both light and air can be necessary for degradation of psilocin).

Photostabilizing agents are used in products that can degrade during manufacturing, storage, or administration because they are sensitive to light and undergo physical or chemical changes due to light. Anastos 2006 has stated that a likely explanation for the degradation of psilocin or psilocybin by light is the dimerization and/or trimerization of the indoles, which is common under acidic conditions. For indoles under acidic conditions, protonation at C3 produces the 3H-indolium cation as the major species; this has been confirmed in solution spectroscopically. 3H-indolium cations are electrophilic and will react with unprotonated indole to form acid dimerisation and trimerisation products. The photostabilizing agent can be, but is not limited to, excipients with spectral overlay (such as Eusolex 9020 [4-(t-butyl-4'-methoxydibenzoyl)-methane], riboflavin, UV absorbers such as 3-(4-methylbenzylidene)-camphor (Eusolex 6300), or α-(o-tolylazo)-β-naphthylamine), food colorants, drug products with opacifying/coating agents (such as yellow, red, and black iron oxides incorporated in tablets, use of opaque blisters and capsules, a dye with an absorption spectrum similar to that of psilocin, use of a reflecting pigment such as titanium dioxide, addition of UV and visible absorbing opacifiers, or a film coating with agents possessing light absorption or reflection properties), or combinations thereof.

Antioxidants can be used to delay or inhibit oxidation of a compound by being preferentially oxidized or blocking an oxidative chain reaction. The antioxidant can be, but is not limited to, ascorbic acid, α-tocopherol acetate, acetone sodium bisulfite, acetylcysteine, ascorbyl palmitate, butylated hydroxyanisole (BHA), butylated hydroxytoluene (BHT), cysteine, cysteine hydrochloride, d-α-tocopherol natural, d-α-tocopherol synthetic, dithiothreitol, monothioglycerol, nordihydroguaiaretic acid, propyl gallate, sodium bisulfite, sodium formaldehyde sulfoxylate, sodium metabisulfite, sodium sulfite, sodium thiosulfate, thiourea, or combinations thereof.

Any of the photostabilizing or antioxidant agents can also work synergistically with the psilocin or provide additional beneficial effects. For example, prebiotics such as lactulose provide antioxidant effects as well as other advantageous effects in pain treatment.

The composition can also use chemical modifications to provide stability, such as pharmaceutical salts or polymorphs. Pharmaceutical salts can be formed with any cations of aluminum, arginine, benzathine, calcium, chloroprocaine, choline, diethanolamine, ethanolamine, ethylenediamine, histidine, lithium, lysine, magnesium, meglumine, potassium, procaine, sodium, triethylamine, or zinc. Pharmaceutical salts can also be formed with any anions of acetate, aspartate, benzenesulfonate, benzoate, besylate, bicarbonate, bitartrate, bromide, camsylate, carbonate, chloride, citrate, decanoate, edetate, estolate, esylate, fumarate, gluceptate, gluconate, glutamate, glycolate, glycollylarsanilate, hexanoate, hexylresorcinate, hydrabamine, hydroxynaphthoate, iodide, isethionate, isethionate, lactate, lactobionate, malate, maleate, mandelate, mesylate, methylbromide, methylnitrate, methylsulfate, mucate, napsylate, nitrate, octanoate, oleate, pamoate, pantothenate, phosphate, polygalacturonate, propionate, salicylate, stearate, subacetate, succinate, sulfate, tartrate, teoclate, tosylate, or triethiodide. Deuterated psilocin can be used to provide stability in which one or more hydrogen atoms in psilocin have been replaced with deuterium atoms.

The composition can also be formed as an acid such as, but not limited to, naphthalene-1,5-disulfonic acid, sulfuric acid, ethane 1,2-disulfonic acid, naphthalene-2-sulfonic acid, benzenesulfonic acid, maleic acid, phosphoric acid, ethanesulfonic, p-toluenesulfonic, methanesulfonic, glutamic, malonic, gentisic, salicylic, citric, malic (including L-malic, D-malic, and DL-malic), lactic (including L-lactic, D-lactic, and DL-lactic), benzoic, succinic, glutaric, hydrochloric, hydrobromic, oxalic, tartaric (including L-tartaric. D-tartaric, and DL-tartaric), fumaric, acetic, L-aspartic, galactaric, glycoloic, hippuric, gluconic, sebacic, adipic, or ascorbic (including L-ascorbic, D-ascorbic, and DL-ascorbic).

The composition can also be stored in any suitable way to prevent degradation from heat, light, air, and/or water.

The present invention therefore provides for a method making stable psilocin, by providing a formulation of psilocin including at least one agent that provides enhanced stability.

The composition can be in a liquid dosage form such as, but not limited to, suspensions, solutions, emulsions, elixirs, tinctures, sprays, syrups, gels, magmas, liniments, lotions, ointments, pastes, drops, or inhalants. The composition can be in a solid dosage form such as, but not limited to, capsules, films, lozenge, patch, powder, tablets, pellets, pills, or troches.

The composition can be administered by any route of administration, such as, but not limited to, oral, intravenous (IV) injection, intramuscular (IM) injection, subcutaneous (SC) injection, intraarterial, intraperitoneal, intratonsillar, intrathecal, infusion, intranasal, sublingual, buccal, rectal, vaginal, ocular, inhalation, nebulization, topical, transdermal, or transmucosal.

Liposome formulations can be used with the composition, including conventional liposomes, PEGylated liposomes, ligand-targeted liposomes, and therapeutic liposomes. Liposomes are phospholipid vesicles of one or more concentric lipid bilayers enclosing discrete aqueous spaces that can encapsulate hydrophilic or hydrophobic drug compositions. Conventional liposomes include a lipid bilayer that can be composed of cationic, anionic, or neutral (phospho)lipids and cholesterol, which encloses an aqueous volume. PEGylated liposomes utilize polyethylene glycol (PEG) to improve liposome stability and enhance their circulation times in the blood. Ligand-targeted liposomes are used for site-specific delivery of drugs to designated cell types or organs in vivo, which selectively express or over-express specific ligands (e.g., receptors or cell adhesion molecules) at the site of disease.

Nanoparticle formulations can also be used with the composition to improve the stability and solubility of the composition, promote transport across membranes, and prolong circulation times to increase safety and efficacy. The nanoparticle formulations can include lipid-based nanoparticles of spherical platforms including at least one lipid bilayer surrounding at least one internal aqueous compartment, which are usually made of phospholipids. Lipid nanoparticles can be used which are made of cationic or ionizable lipids that complex with negatively charged genetic material and aid endosomal escape, phospholipids for particle structure, cholesterol for stability and membrane fusion, and PEGylated lipids to improve stability and circulation. Polymeric nanoparticles (including nanocapsules and nanospheres) can be used made from natural or synthetic materials, monomers, or preformed polymers, and the composition can be encapsulated within the core, entrapped in the polymer matrix, chemically conjugated to the polymer, or bound to the surface. Inorganic nanoparticles using gold, iron, or silica can be used.

The compound of the present invention is administered and dosed in accordance with good medical practice, considering the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

The patient being treated is a warm-blooded animal and, in particular, mammals including man. The pharmaceutically acceptable carriers, diluents, adjuvants, and vehicles as well as implant carriers generally refer to inert, non-toxic solid or liquid fillers, diluents or encapsulating material not reacting with the active ingredients of the invention.

The doses can be single doses or multiple doses over a period of several days. The treatment generally has a length proportional to the length of the disease process and drug effectiveness and the patient species being treated.

When administering the compound of the present invention parenterally, it will generally be formulated in a unit dosage injectable form (solution, suspension, emulsion). The pharmaceutical formulations suitable for injection include sterile aqueous solutions, other solutions, or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

Psilocin acts as a 5HT2A, 5HT2C, and 5HT1A agonist or partial agonist and can be administered for any condition or disease that psilocybin is administered for. The condition or disease can include, but is not limited to, anxiety disorders (including anxiety in advanced stage illness e.g. cancer, as well as generalized anxiety disorder), depression (including post partum depression, major depressive disorder and treatment-resistant depression), headache disorder (including cluster headaches and migraine headache), obsessive compulsive disorder (OCD), personality disorders (including conduct disorder), stress disorders (including adjustment disorders and post-traumatic stress disorder), drug disorders (including alcohol dependence, nicotine dependence, opioid dependence, cocaine dependence, methamphetamine dependence), other addictions (including gambling disorder, eating disorder, and body dysmorphic disorder), pain, neurodegenerative disorders (such as dementia, Alzheimer's Disease, Parkinson's Disease), autism spectrum disorder, eating disorders, or neurological disorders (such as stroke).

Therefore, the present invention provides for a method of treatment of a disease or condition, by administering a composition of psilocin that is stable, and treating the disease or condition.

The invention is further described in detail by reference to the following experimental examples. These examples are provided for the purpose of illustration only and are not intended to be limiting unless otherwise specified. Thus, the invention should in no way be construed as being limited to the following examples, but rather, should be construed to encompass any and all variations which become evident as a result of the teaching provided herein.

Example 1

PK Evaluation of Psilocin and Psilocybin after IV and PO Administration in Rats

Study Design

The study design is shown in FIGS. 1A and 1B. The study was conducted in male/female CD rats. Test articles were formulated fresh in PBS. Psilocin and Psilocybin were administered IV and PO. Plasma samples were analyzed for psilocin and psilocybin (group 2).

Figure 4B:
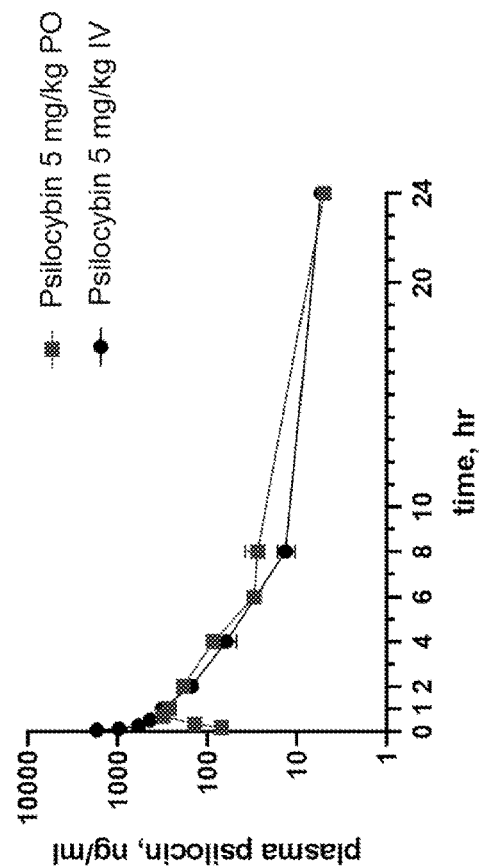
FIG. 4B is a graph showing psilocybin administered IV and PO.
Figure 4A:
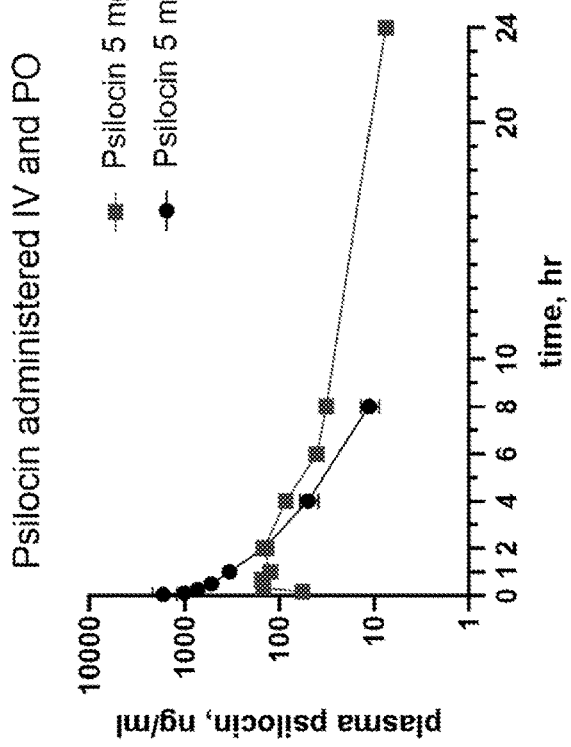
FIG. 4A is a graph showing psilocin administered IV and PO.

FIGS. 2A-2C show PK characteristics of psilocin and psilocybin after IV dosing. FIGS. 3A-3B show PK characteristics of psilocin and psilocybin after PO dosing. FIGS. 4A-4B show psilocin and psilocybin after IV and PO dose. FIG. 5 shows dosing solution analyses.

Conclusions

IV administration of psilocin (free base) and psilocybin results in almost identical PK values, including $C_{max}$ and AUC and Cl. After IV administration, psilocybin is detectable in plasma for 15 minutes. PO administration of psilocin and psilocybin results in similar PK values, including $t_{max}$, $t_{1/2}$, AUC, and bioavailability. Measured $C_{max}$ after administration of psilocybin is higher (313.7 mg/ml) compared to 152.7 ng/ml after administration of psilocin. Low stability of psilocin in aqueous solutions could be a contributing factor to observed differences. Analytical characterization of dosing solutions used in the PK study, after 2 hours on the bench at room temperature demonstrates that psilocin solutions have approximately 30%-70% degradation, depending on the concentration. Stabilization of psilocin provides viable, stable formulations and lower variability of dosing solutions, resulting in a better PK, such as compared to psilocybin.

Example 2

Analytical Characterization of a Psilocin Tartrate Sample

Figure 6:
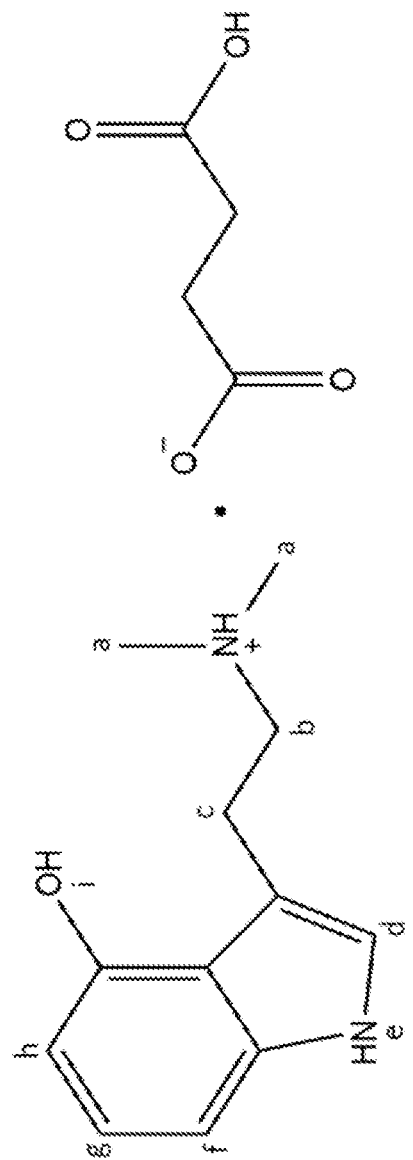
FIG. 6 shows the chemical structure of psilocin tartrate.
Figure 7D:
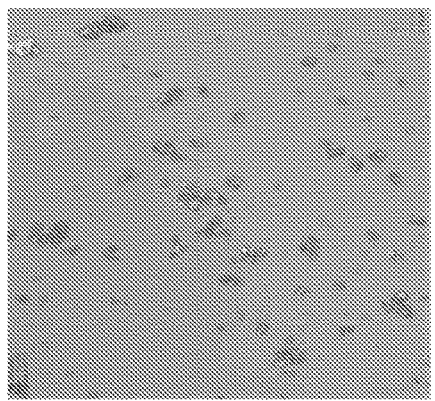
FIG. 7D is an OM image.
Figure 7C:
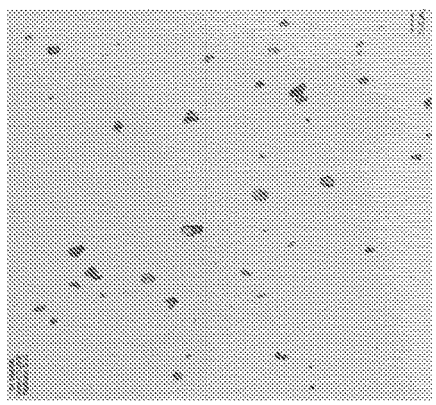
FIG. 7C is an OM image.
Figure 7B:
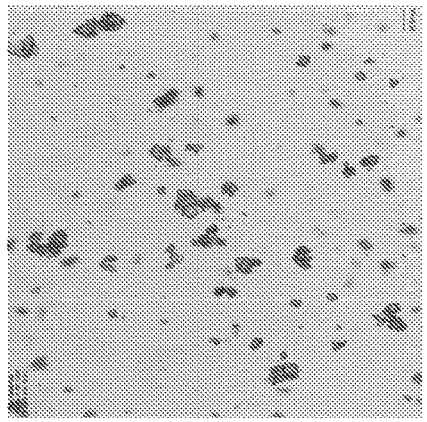
FIG. 7B is an OM image.
Figure 7A:
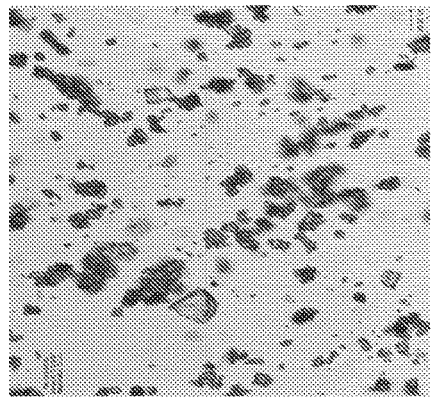
FIG. 7A is an OM image.
Figure 7F:
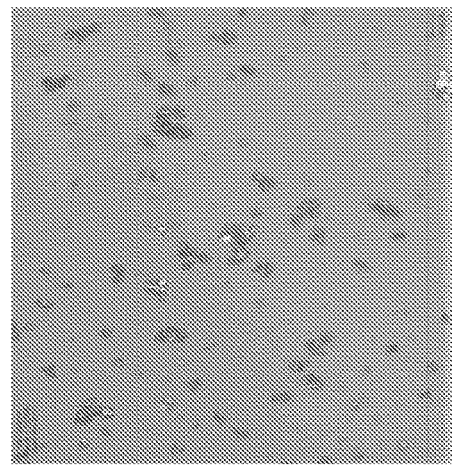
FIG. 7F is an OM image.
Figure 7E:
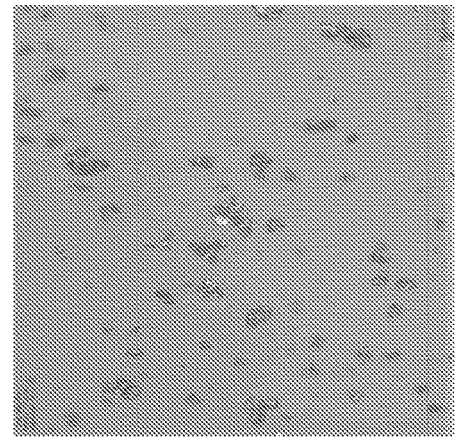
FIG. 7E is an OM image.

One sample of psilocin tartrate (lot 16782-15C) was submitted for optical microscopy (OM), X-ray powder diffraction (XRPD), differential scanning calorimetry (DSC), thermogravimetric analysis (TGA), dynamic vapor sorption/desorption (DVS), and $^1$H NMR spectroscopy. The chemical structure of psilocin is displayed in FIG. 6. The data in this EXAMPLE shows that psilocin tartrate is a stable crystalline solid.

Results

FIGS. 7A-7F show the OM images for psilocin tartrate lot 16782-15C. The sample contains particles that are agglomerates in various shapes. The agglomerates range in length from ~20 to 50 micrometers. Images of the agglomerates that were obtained with crossed polars in place show birefringence with extinction indicating that these particles are crystalline.

Figure 8:
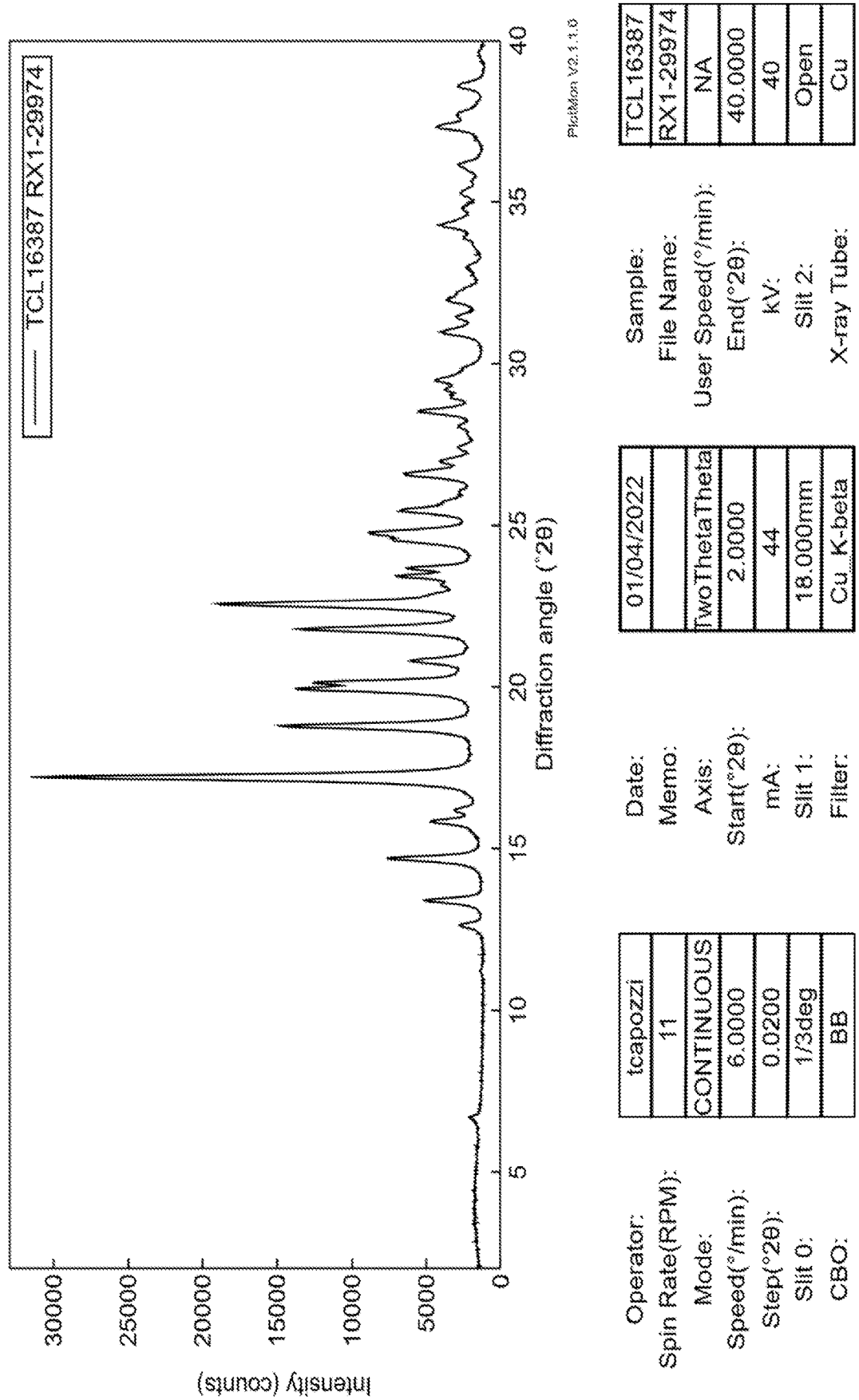
FIG. 8 is a graph of XPRD pattern for psilocin tartrate (initial material)
Figure 9:
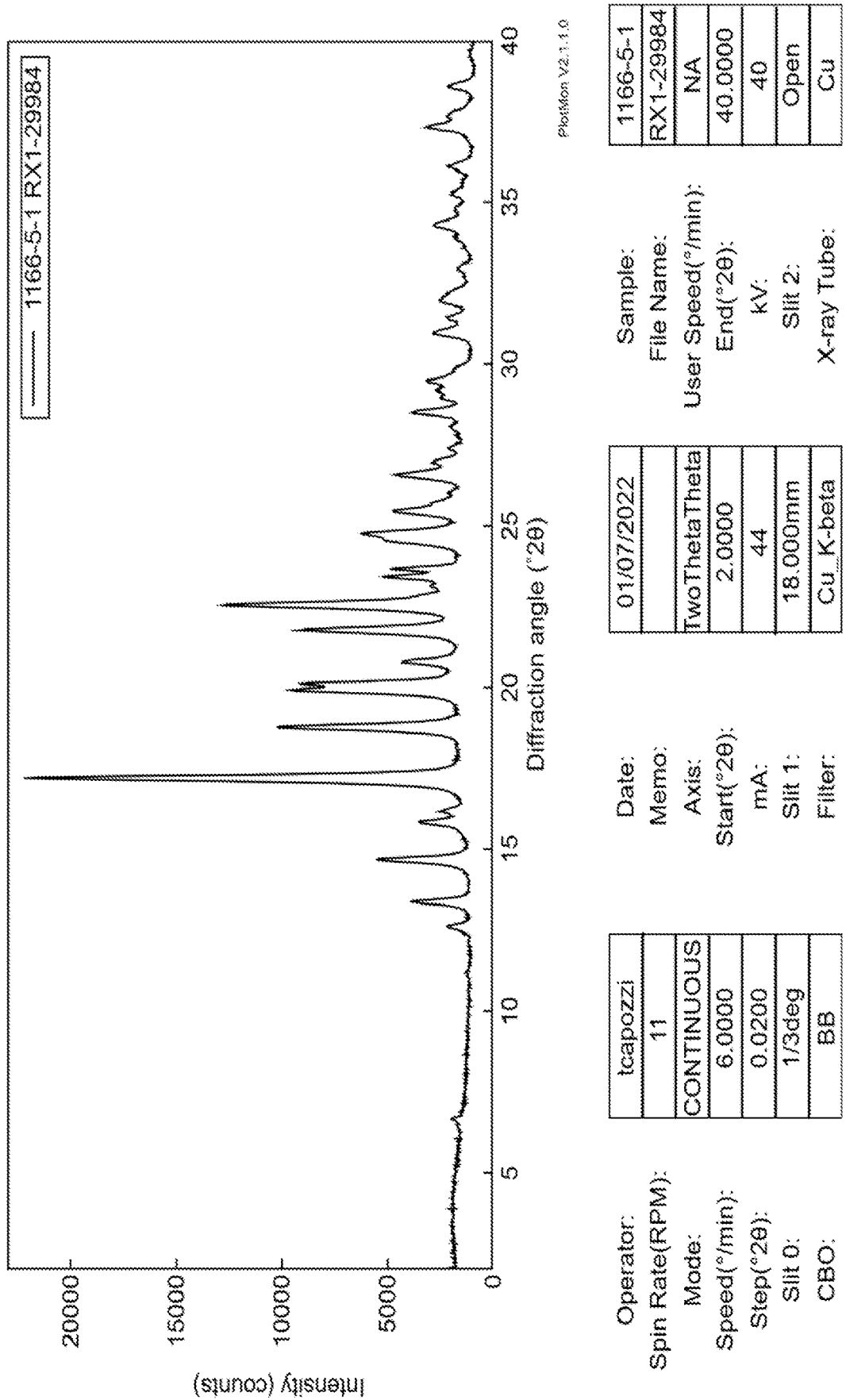
FIG. 9 is a graph of XPRD pattern for psilocin tartrate (post DVS analysis)
Figure 10:
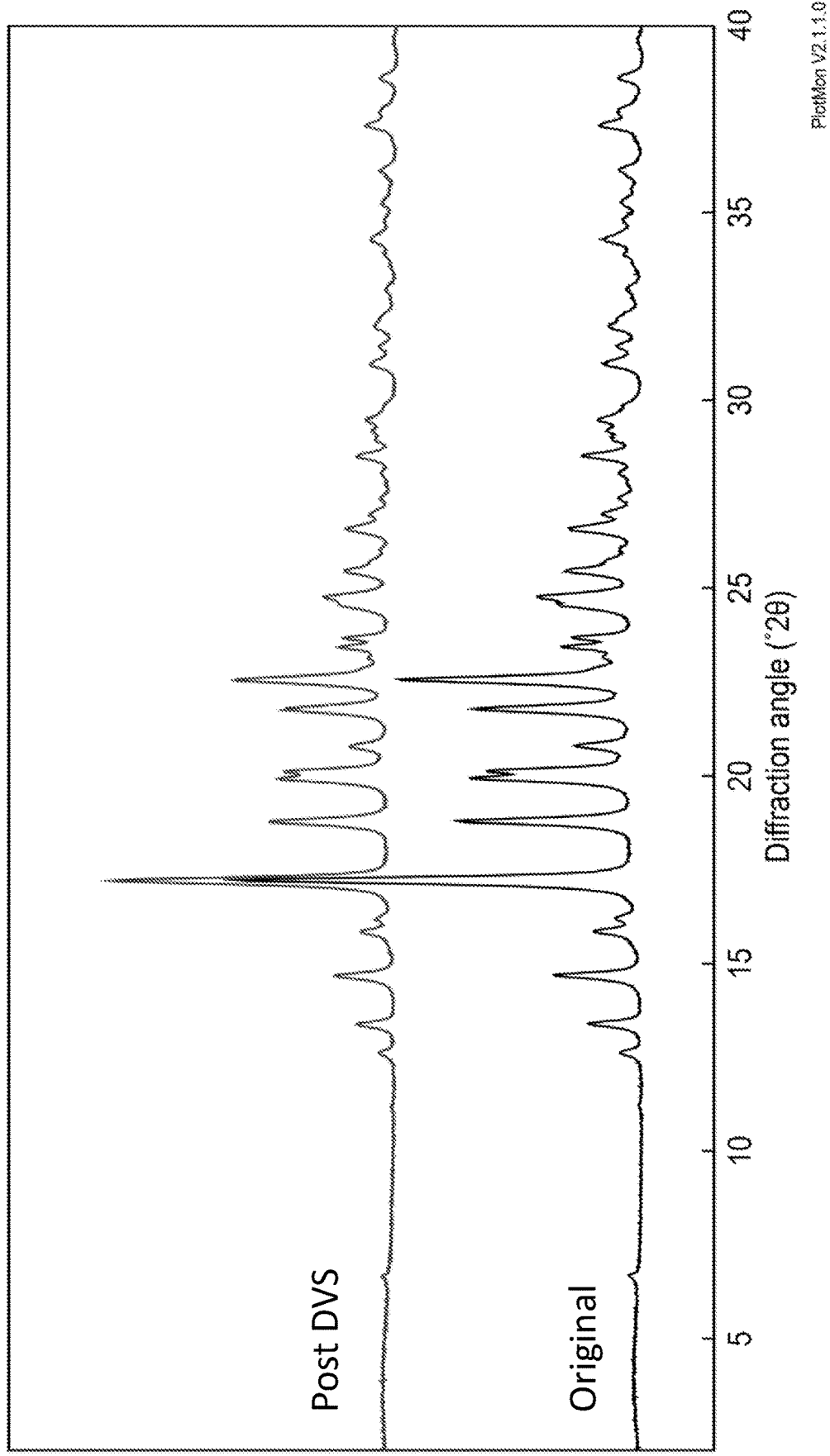
FIG. 10 is a stack plot of the patterns for psilocin tartrate (post DVS and original material)

The acquired XRPD patterns for psilocin tartrate, initial material, and post DVS analysis, are presented in FIGS. 8 and 9, respectively. Based upon the observance of sharp and discrete peaks, the materials are crystalline in nature. A stack plot of the two XRPD patterns is presented in FIG. 10. A visual comparison of the patterns shows that the patterns correspond indicating the same form or mixture of forms is in each material. A list of diffraction peaks for psilocin tartrate lot 16782-15C is displayed in TABLE 1.

TABLE 1

XRPD Peak List for Psilocin Tartrate Lot 16782-15C

| No. | Peak Position (°2θ) | Height (cps) | Relative Height |
|---|---|---|---|
| 1 | 6.6713 | 437 | 2.24 |
| 2 | 11.2219 | 144 | 0.74 |
| 3 | 12.6191 | 1068 | 5.48 |
| 4 | 13.3782 | 2592 | 13.31 |
| 5 | 14.6880 | 4173 | 21.43 |
| 6 | 15.8348 | 1984 | 10.19 |
| 7 | 16.2121 | 882 | 4.53 |
| 8 | 17.2119 | 19472 | 100.00 |
| 9 | 18.7798 | 8512 | 43.71 |
| 10 | 19.9341 | 7290 | 37.44 |
| 11 | 20.1303 | 6674 | 34.27 |
| 12 | 20.7831 | 2425 | 12.46 |
| 13 | 21.7831 | 7093 | 36.43 |
| 14 | 22.5575 | 11129 | 57.15 |
| 15 | 23.4041 | 2576 | 13.23 |
| 16 | 23.6627 | 2544 | 13.07 |
| 17 | 24.5334 | 2529 | 12.99 |
| 18 | 24.7431 | 3746 | 19.24 |
| 19 | 25.4678 | 2480 | 12.73 |
| 20 | 26.5473 | 2549 | 13.09 |
| 21 | 26.9630 | 1098 | 5.64 |
| 22 | 27.3972 | 464 | 2.38 |
| 23 | 28.0135 | 506 | 2.60 |
| 24 | 28.4814 | 2352 | 12.08 |
| 25 | 28.9430 | 789 | 4.05 |
| 26 | 29.1422 | 1062 | 5.46 |
| 27 | 29.4225 | 1512 | 7.77 |
| 28 | 30.9344 | 1601 | 8.22 |
| 29 | 31.4133 | 968 | 4.97 |
| 30 | 31.9523 | 769 | 3.95 |
| 31 | 32.1452 | 918 | 4.71 |
| 32 | 33.0004 | 433 | 2.22 |
| 33 | 33.9094 | 523 | 2.69 |
| 34 | 34.2194 | 1564 | 8.03 |
| 35 | 34.7791 | 583 | 2.99 |
| 36 | 35.1879 | 672 | 3.45 |
| 37 | 36.1506 | 841 | 4.32 |
| 38 | 37.3310 | 2076 | 10.66 |
| 39 | 37.6760 | 1037 | 5.33 |
| 40 | 38.5589 | 1192 | 6.12 |

Figure 11:
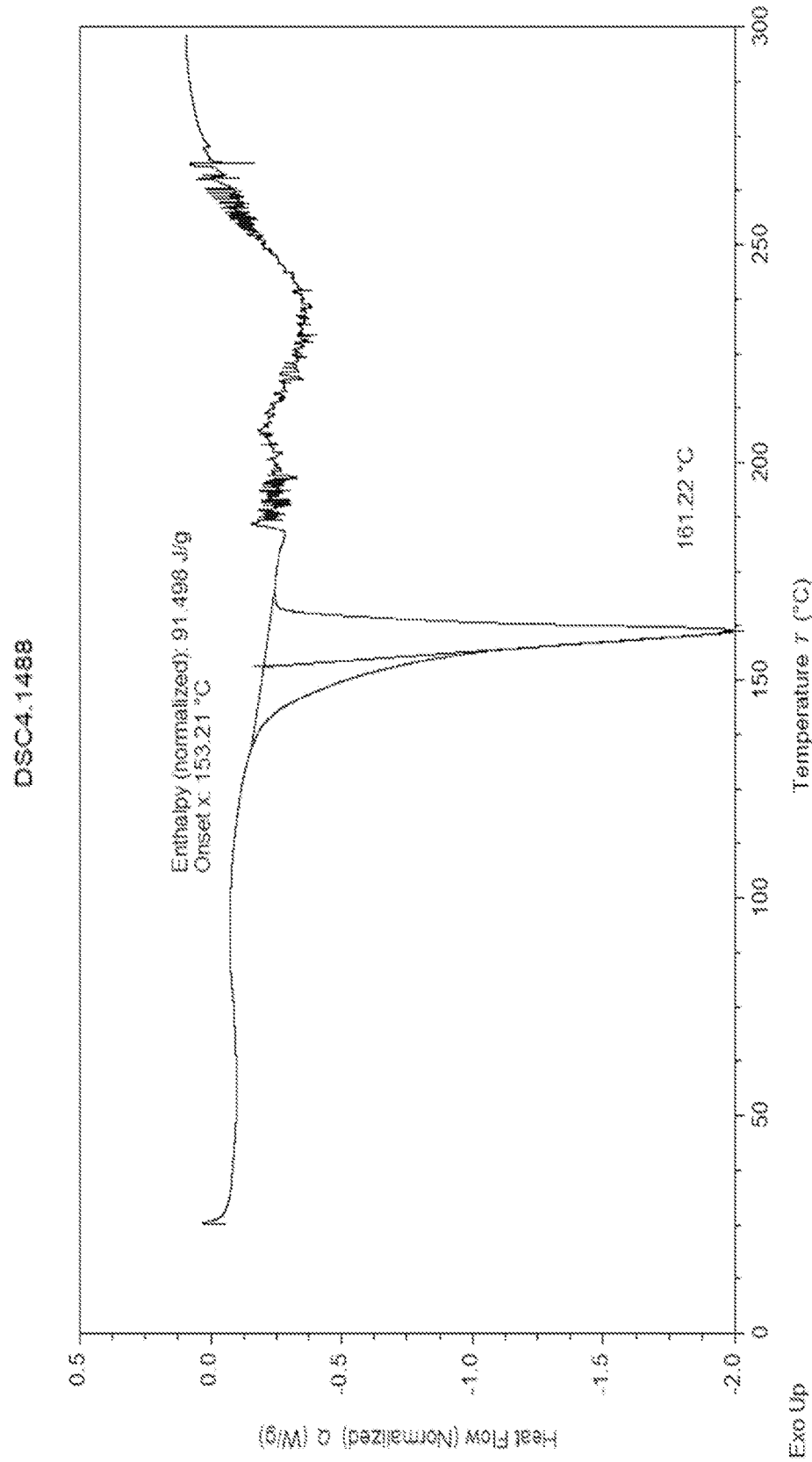
FIG. 11 is an annotated DSC thermogram for psilocin tartrate.

The annotated DSC thermogram for the psilocin tartrate lot 16782-15C is presented in FIG. 11. The DSC thermogram displays an endothermic event at 161.22° C., which appears to be a melting event. The thermal event starting at ~180° C. is most likely decomposition as it is consistent with the rapid weight loss observed in the TGA.

Figure 12:
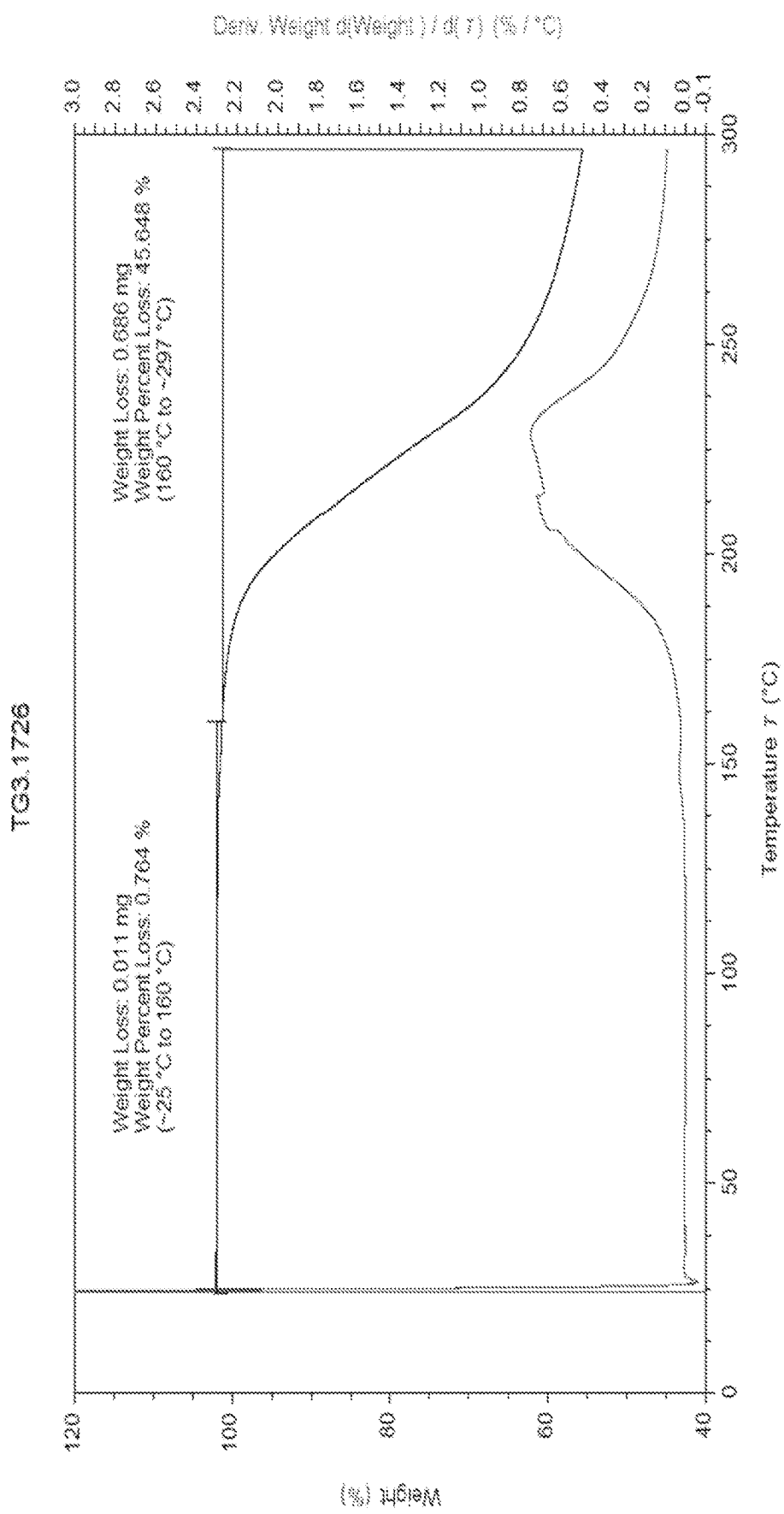
FIG. 12 is an annotated TGA curve for psilocin tartrate, with first derivative of the weight loss curve.

The annotated TGA curve for the psilocin tartrate lot 16782-15C is presented in FIG. 12. The first derivative curve has been added to help determine the endpoint of the weight losses. The first minimal weight loss event, 0.76% up to 160° C., is likely related to volatile loss. The more rapid weight loss event from 160° C. to ~297° C. of 45.65% appears to be decomposition.

Figure 13:
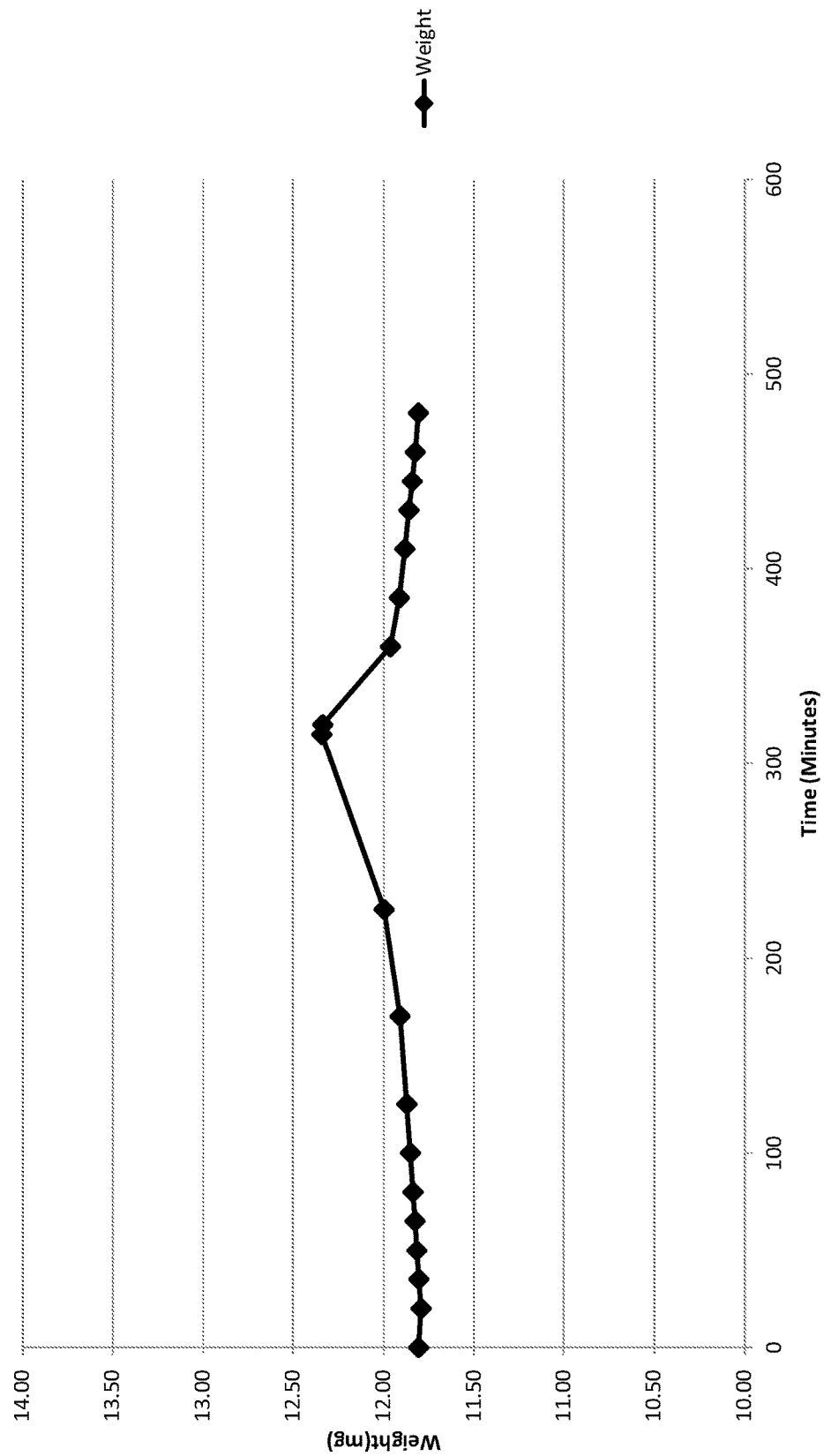
FIG. 13 is a graph of weight versus time for psilocin tartrate.
Figure 14:
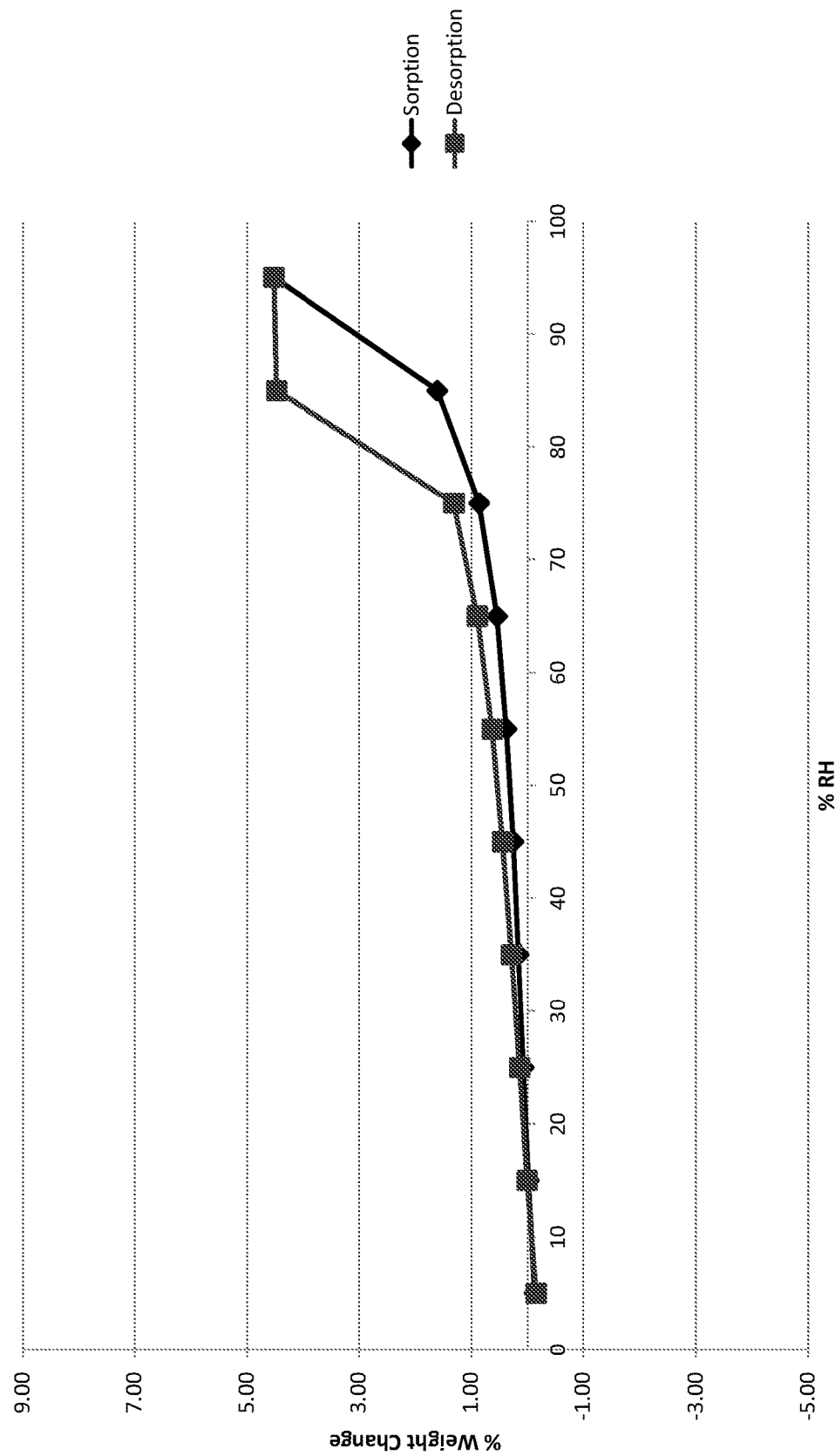
FIG. 14 is a graph of percent weight change versus percent relative humidity plot for psilocin tartrate.

The weight versus time and percent weight change versus percent relative humidity (RH) curves from the DVS analysis of psilocin tartrate lot 16782-15C is presented in FIGS. 13 and 14, respectively. The data show that the sample takes up water suggesting that the sample is moderately hygroscopic and exhibited some hysteresis between the 80-95% RH range. The results are listed in TABLE 2.

TABLE 2

Summary of DVS Results

| Lot Number | DVS Results |
|---|---|
| 16782-15C | 0.12% wt. loss upon equilibration at 5% RH |
| | 4.64% wt. gain from 5 to 95% RH |
| | 4.67% wt. loss from 95 to 5% RH |

Figure 15:
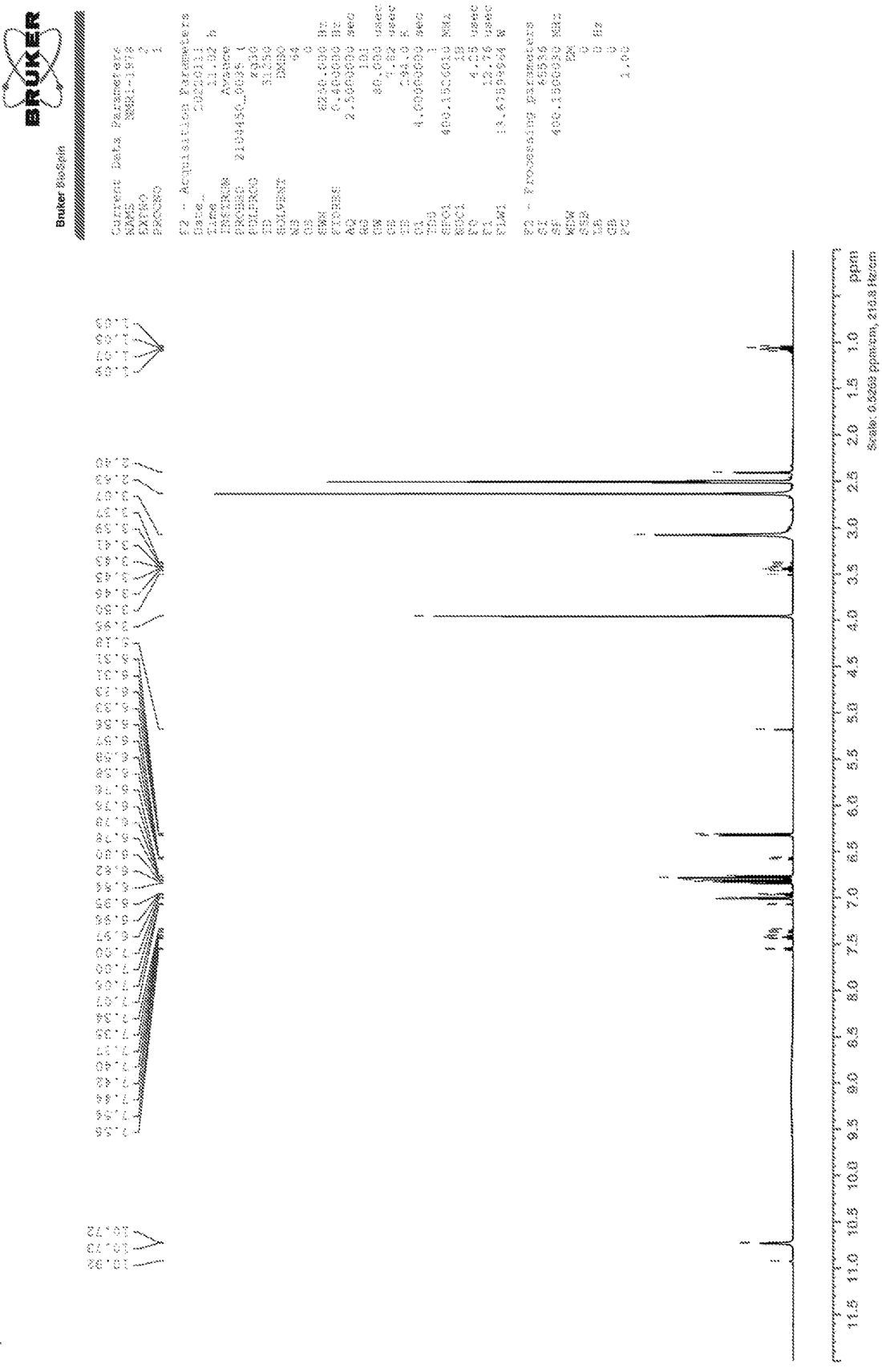
FIG. 15 is a $^1$H NMR spectrum of psilocin tartrate.
Figure 16:
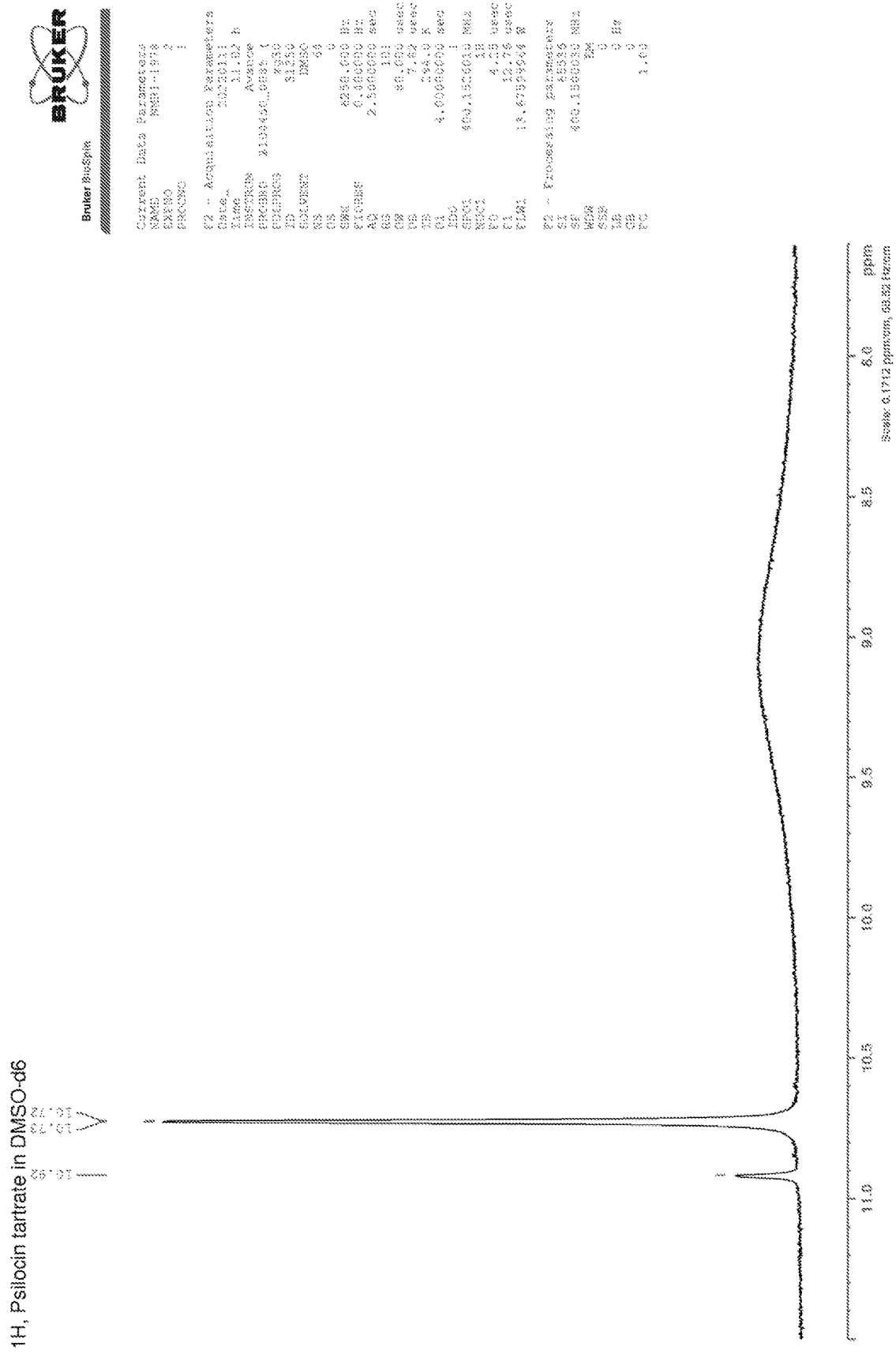
FIG. 16 is an expanded $^1$H NMR spectrum of psilocin tartrate (7.6-11.5 ppm)
Figure 17:
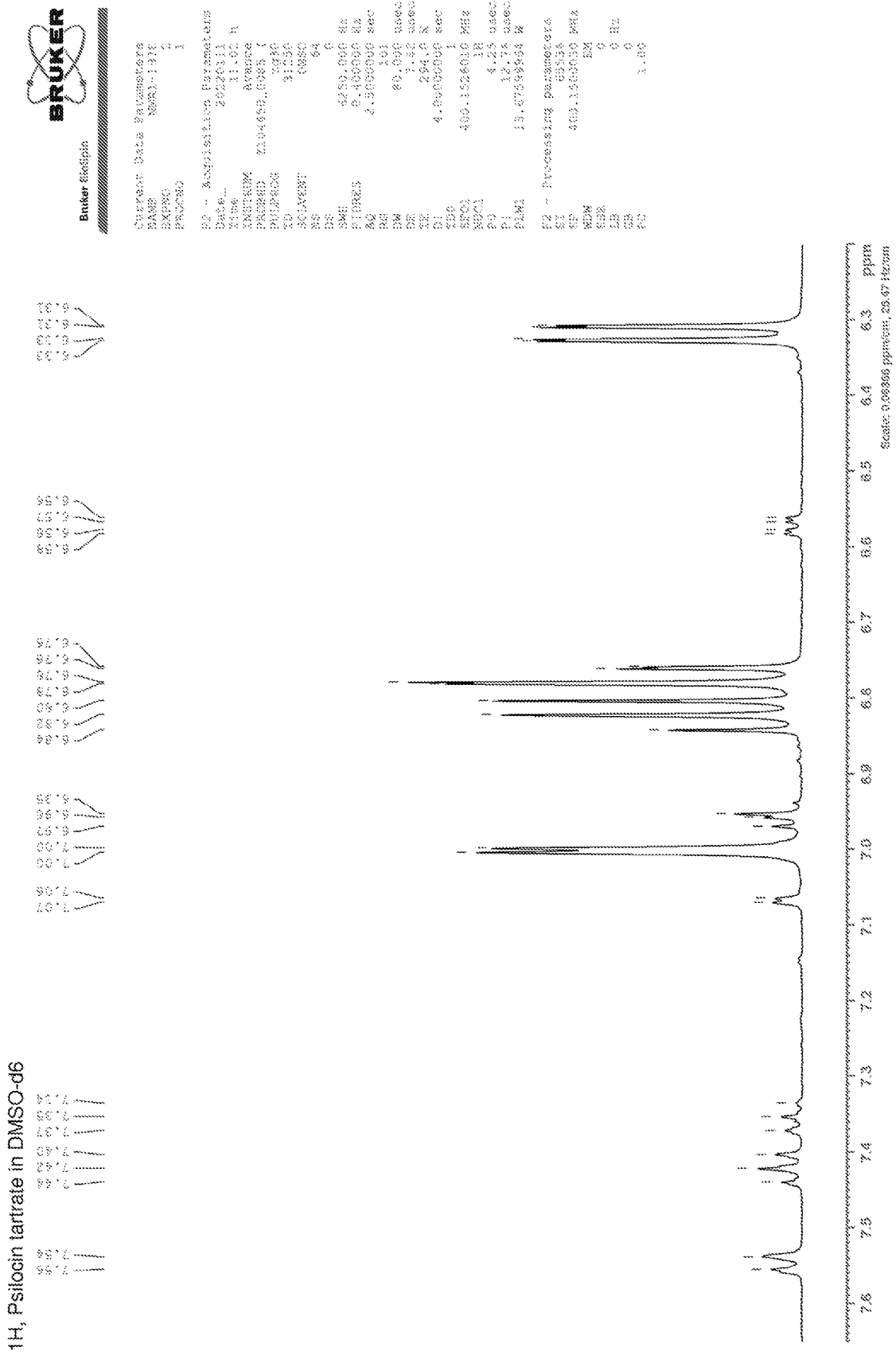
FIG. 17 is an expanded $^1$H NMR spectrum of psilocin tartrate (6.2-7.65 ppm)
Figure 18:
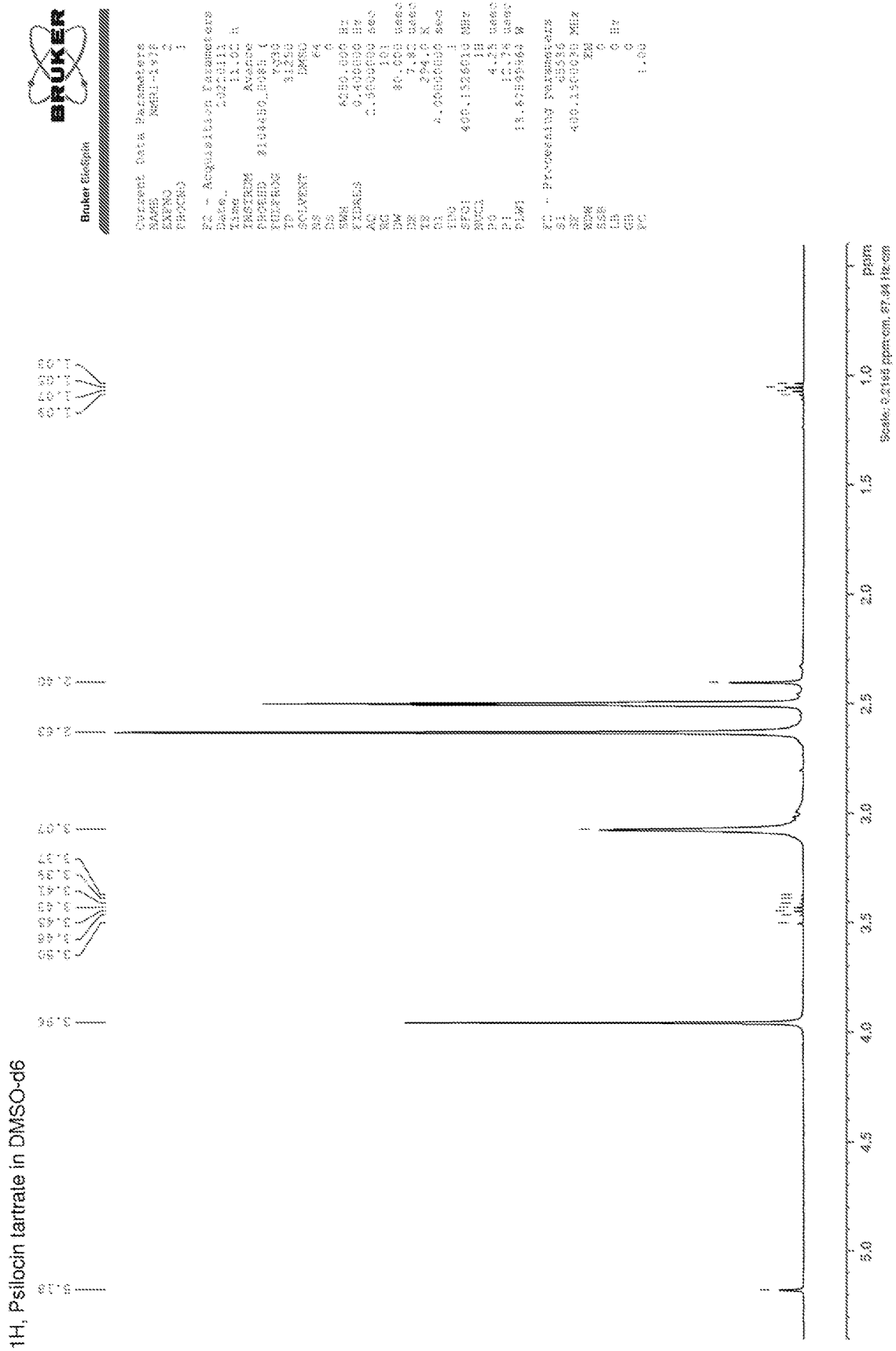
FIG. 18 is an expanded $^1$H NMR spectrum of psilocin tartrate (0.8-5.4 ppm)
Figure 19:
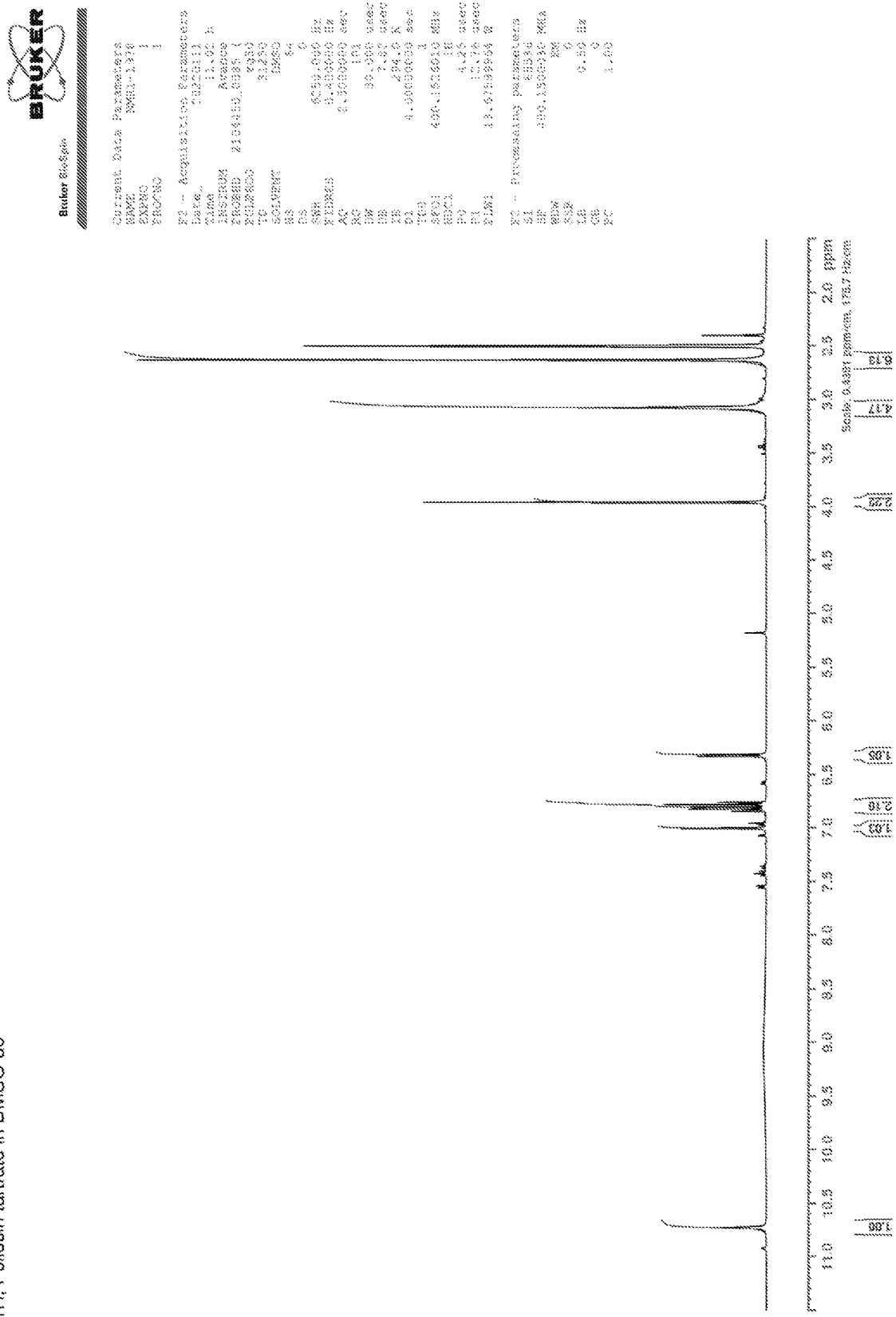
FIG. 19 is a $^1$H NMR spectrum of psilocin tartrate with integrations.

The $^1$H NMR spectrum (NMR1-1978) of psilocin tartrate lot 16782-15C is shown in FIG. 15 with expanded plots in FIGS. 16-19. The $^1$H chemical shift assignments for psilocin tartrate (as labeled in FIG. 6) were performed and indicated in each spectrum except for unidentified $^1$H signals, which may be attributed to impurities in the sample.

Experimental

XRPD

The samples were prepared in a silicon low background holder using light manual pressure to keep the sample surface flat and level with the reference surface of the sample holder. The single crystal Si low background holder has a circular recess (10 mm diameter and about 0.2 mm depth) that holds the sample.

The Rigaku Smart-Lab diffraction system used was configured for Bragg-Brentano reflection geometry using a line source X-ray beam. The Bragg-Brentano geometry was controlled by passive divergence and receiving slits with the sample itself acting as the focusing component for the optics. Data collection parameters are shown in TABLE 3.

TABLE 3

Data Collection Parameters

| Parameter | Value | Parameter | Value |
|---|---|---|---|
| Geometry | Bragg-Brentano | Receiving Slit 1 (mm) | 18 |
| Tube Anode | Cu Kα | Receiving Slit 2 (mm) | open |
| Tube Type | Long Fine Focus | Start Angle (°2θ) | 2 |
| Tube Voltage (kV) | 40 | End Angle (°2θ) | 40 |
| Tube Current (mA) | 44 | Step Size (°2θ) | 0.02 |
| Detector | D/teX Ultra 250 | Scan Speed (°2θ/min) | 6 |
| Monochromatization | Kβ Filter | Spinning (rpm) | 11 |
| Incident Slit (°) | 1/3 | Sample Holder | Large well silicon low background holder |

DSC

DSC analysis was performed using a TA Instruments Discovery Series 2500 DSC instrument. The instrument temperature calibration was performed using indium. The DSC cell was kept under a nitrogen purge of ~50 mL per minute during the analysis. The sample was placed in a standard crimped T-zero aluminum pan covered with a lid. The sample was heated from ambient to 300° C. at a rate of 10° C. per minute. The instrument was controlled with, and software and the data were analyzed with TRIOS v. 5.0.0.44608.

TGA

TG analysis was performed using a TA Instruments Discovery 5500 TGA instrument. The instrument balance was calibrated using class M weights and temperature calibration was performed by the measurement of the Curie point of Alumel® and Nickel. The nitrogen purge was about 10 mL per minute at the balance and about 25 mL per minute at the furnace. Approximately 2 mg of the sample was loaded onto tared, platinum sample pan. During analysis, the sample was heated from ambient temperature to 300° C. at a rate of 10° C./minute. The instrument was controlled with, and software and the data were analyzed with TRIOS v. 5.0.0.44608.

Dynamic Vapor Sorption (DVS) Analysis

DVS analysis was carried out using a TA Instruments Q5000 Dynamic Vapor Sorption analyzer. The instrument was calibrated with standard weights and a sodium bromide standard for humidity. Approximately 12 mg of the powder sample was loaded into a metal-coated quartz pan for analysis. The sample was analyzed at 25° C. after being equilibrated to 5%1=1H in 10% RH steps from 5 to 95% RH (adsorption cycle) and from 95 to 5% RH (desorption cycle). The movement from one step to the next occurred either after satisfying the equilibrium criterion of 0.01% weight change in 5 minutes or, if the equilibrium criterion was not met, after 90 minutes. The percent weight change values were calculated using Microsoft Excel® 2016.

Optical Microscopy (OM)

OM was conducted using a Keyence VHX-2000E digital microscope equipped with a VH-Z20R variable magnification lens assembly (20-200×). The sample particles were illuminated with reflected light. Photo-micrographs at high and low magnifications were acquired and processed using the VHX communication v2.35 software.

$^1$H NMR

The $^1$H NMR spectrum was acquired on a Bruker NEO 400 MHz (9.4 T) spectrometer using TopSpin v4.1.1 software. Psilocin tartrate (3.2 mg) was dissolved in 0.75 mL of DMSO-$d_6$, transferred into a 5-mm NMR tube for subsequent data acquisition. Each spectrum was processed using TopSpin v4.1.1 and referenced to the chemical shift of the residual DMSO-$d_6$ (2.5 ppm). Detailed acquisition parameters are listed in TABLE 4.

TABLE 4

NMR Acquisition Parameters

| Parameter Name | Parameter Value |
|---|---|
| Transmitter Frequency | 400.15 MHz |
| Acquisition Time | 2.5 sec |
| Spectral Width | 6250 Hz |
| Number of Scans | 32 |
| Sequence | ZG30 |
| P1 (pulse width) | 12.8 μsec |
| PLW1 (pulse power) | 13.7 W |
| D1 (relaxation delay) | 4 sec |
| Line Broadening | 0.5 Hz |

Example 3

Figure 21:
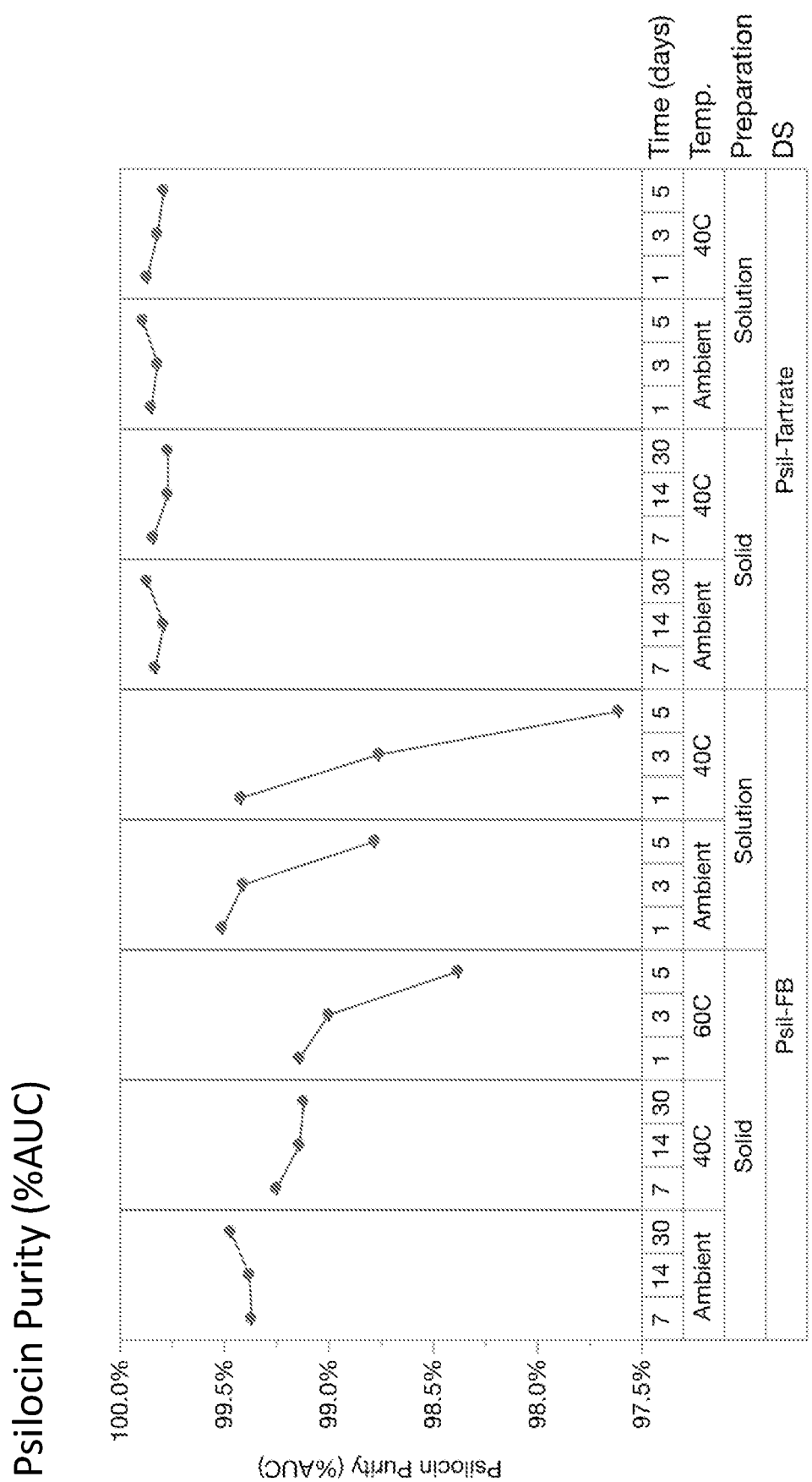
FIG. 21 is a graph of HPLC data.

In this EXAMPLE, the data shows that making a salt is a viable strategy to prepare stable psilocin solution formulations; this can be used to prepare solid psilocin formulations with enhanced shelf life and can lead to improved PK properties upon human dosing. The limited stability of psilocin free base under a variety of stress conditions is shown in the chart in FIG. 20. HPLC data in FIG. 21 shows the improved stability of psilocin tartrate salt compared to the free base in solution. A salt screen using solutions in ethanol is summarized in TABLE 5. TABLE 5 shows that not all acids lead to stable salt formation under the same conditions.

TABLE 5

| Vial # | Acid | Results at 18 h[a,b] | Result at 6 days |
|---|---|---|---|
| 1 | Adipic | V | ↑C |
| 2 | Ascorbic | 0 | C + solid |
| 3 | t-Cinnamic | P | NC |
| 4 | Fumaric | F [c] | 0 + X |
| 5 | Glycolic | F [c] | ↑C |
| 6 | DL-Lactic | F [c] | ↑C |
| 7 | Maleic | 0 | ↑C |
| 8 | Malonic | F [c] | ↑C |
| 9 | Mandelic | 0 | NC |
| 10 | Methanesulfonic | NC | NC |
| 11 | Oxalic | 0 | 0 + X |
| 12 | Salicylic | 0 | ↑C |
| 13 | Succinic | F [c] | ↑C |

TABLE 5-continued

| Vial # | Acid | Results at 18 h[a,b] | Result at 6 days |
|---|---|---|---|
| 14 | L-Tartaric | 0 [d] | 0 + X |
| 15 | p-Toluenesulfonic | NC | NC |
| 16 | Control | P [f] | NC |

Figure 22:
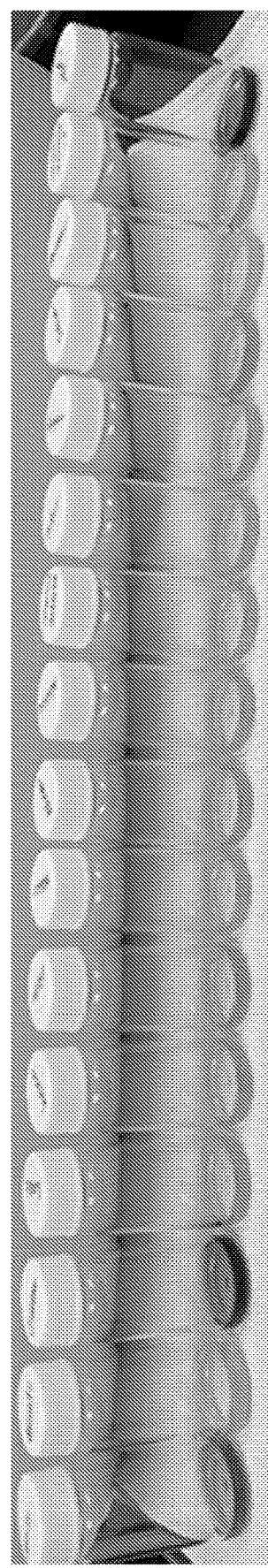
FIG. 22 is a photo showing stability of salt formations of psilocin free base.
Figure 23:
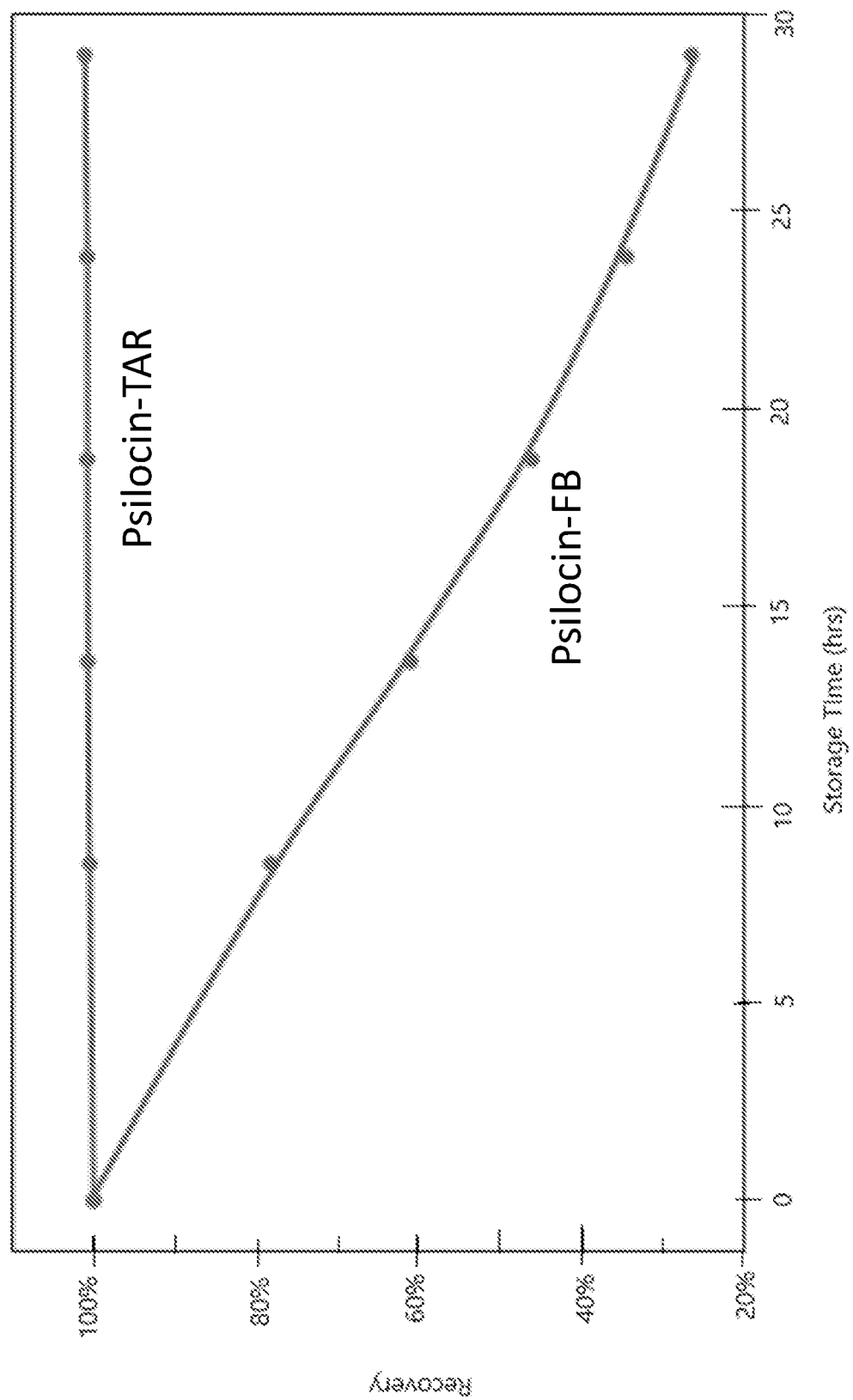
FIG. 23 is a graph of HPLC solution stability data.
Figure 24:
FIG. 24 is a photo showing stability of psilocin free base (left) and psilocin tartrate salt (right)

TABLE 5 key:
[a] T0; after storage overnight at RT (Ar; light-protected); after recording appearances, solvent was removed from each vial (Rotavap), which was then flushed with Ar and stored at RT (light-protected)
[b] see photo in FIG. 22. Vials (left-to-right) contain acids listed in descending order
[c] faint color; DL-Lactic > glycolic = fumaric = malonic = succinic
[d] white ppt present
[e] filtrate
[f] Control > t-cinnamic
[g] T1 (day 1); deepening color/development of color not evident (NC); there were no noticeable changes at T2 (day 2)
[h] appearances recorded after addition of 200 mL EtOH
0 = colorless solution
F = faintly colored solution
P = purple solution
V = violet solution
CS = colored solution
↑ = deeper color
X = crystals present FIG. 22 was taken at an 18-hour timepoint and demonstrates visually that salt formation is effective at improving the stability of psilocin.

Example 4

A salt screen was performed on psilocin. The salt screen was performed according to the saturated API solution method. 23 counterions were explored in 3 solvent systems. For each counterion, 1.1 molar equivalent was used. In case the counterion had multiple ionization sites, 0.55 molar equivalent was also tested. To (close to) saturated solution of the API in ethanol, acetonitrile, and methyl ethyl ketone, 1M solutions of the counterion was added. With ACN solutions, aqueous counterion solutions were used, and with EtOH and MEK, counterion solutions prepared in THF were used. The mixtures were kept at RT overnight and than equilibrated at 5° C. for 3 days. Solids and liquids were separated. Solids were analyzed by XRPD wet and after drying under vacuum. The solvents were evaporated and obtained solids were analyzed by XRPD.

Figures 25A, 25B:
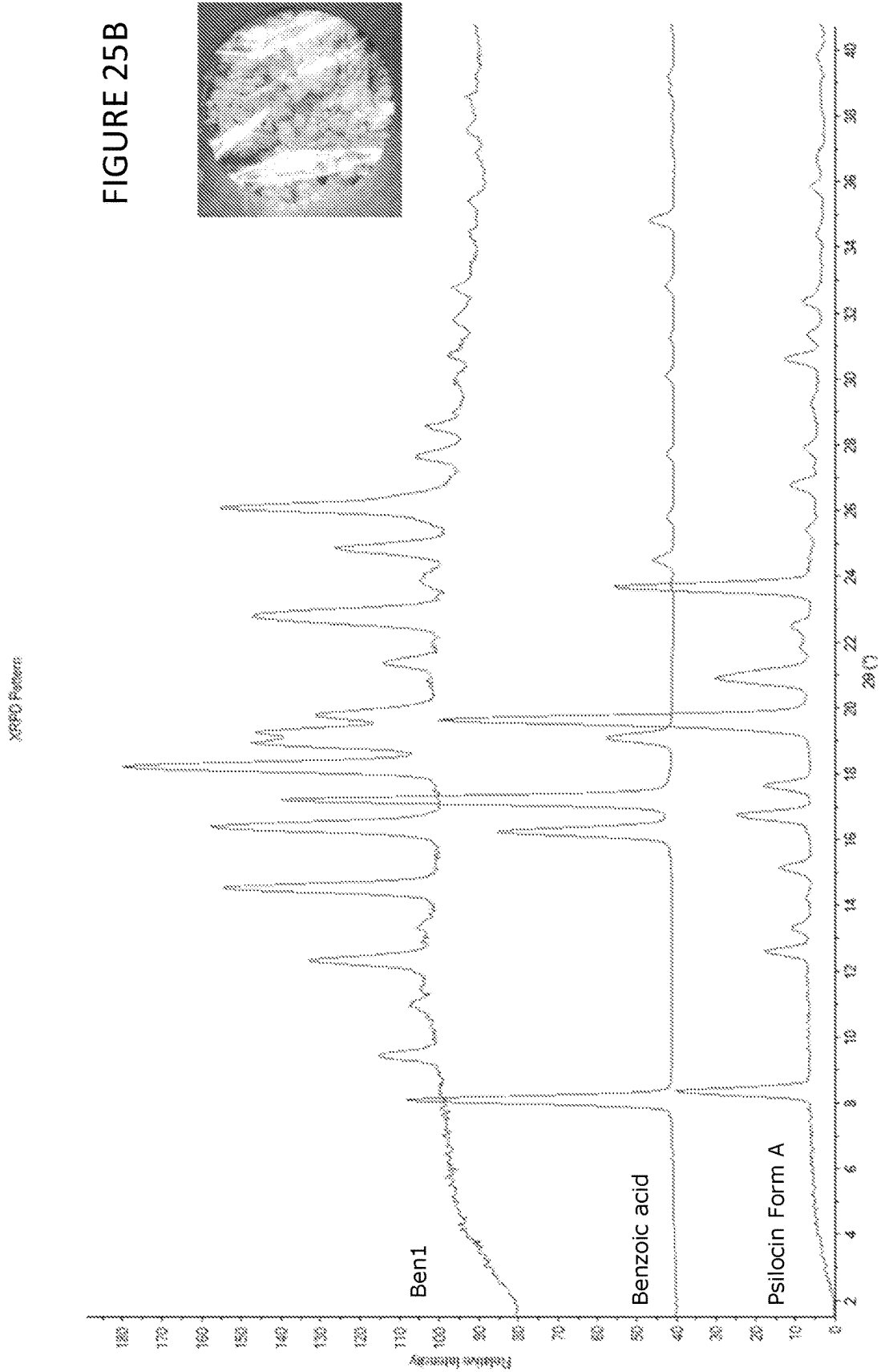
FIG. 25A is a graph of XRPD pattern of benzoate salt (Ben1) and FIG. 25B is a photograph showing the vacuum dried benzoate salt.

A benzoate salt was recovered. FIG. 25A shows XRPD patterns of benzoate salt Ben1 compared to psilocin free base and benzoic acid. FIG. 25B shows the vacuum dried benzoate salt.

Figure 26A:
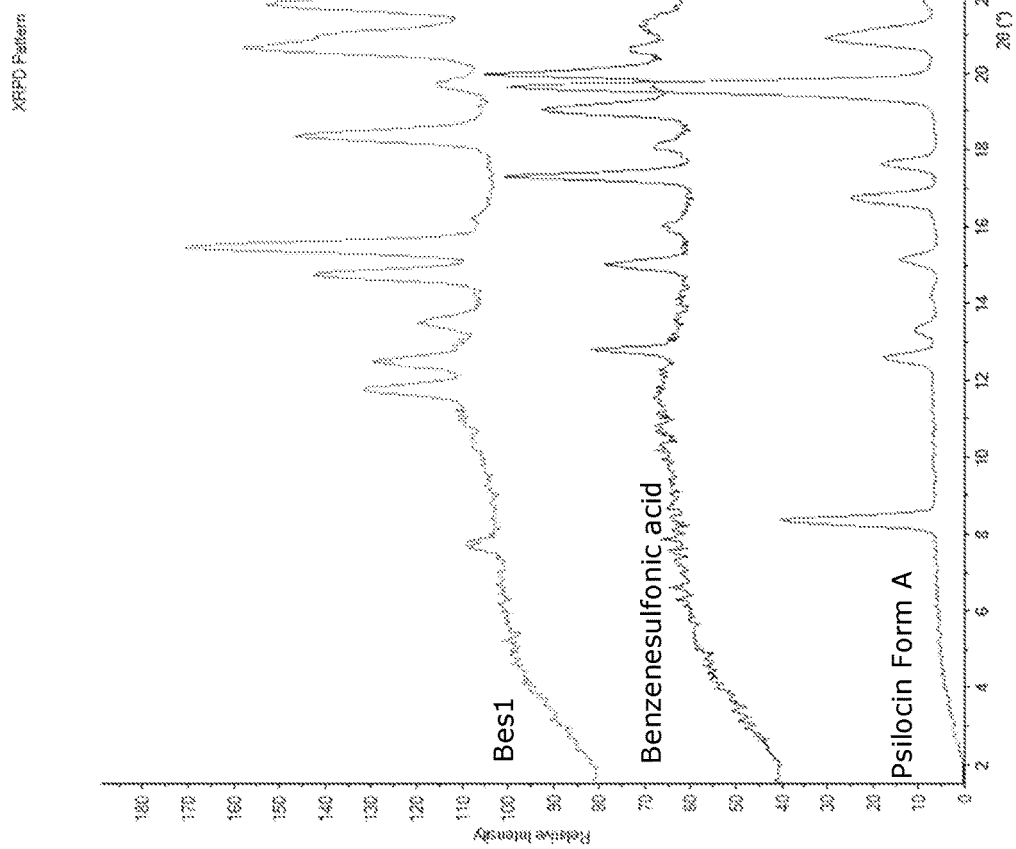
FIG. 26A is a graph of XRPD pattern of besylate salt (Bes1) and FIG. 26B is a photograph showing the vacuum dried besylate salt.
Figure 26B:
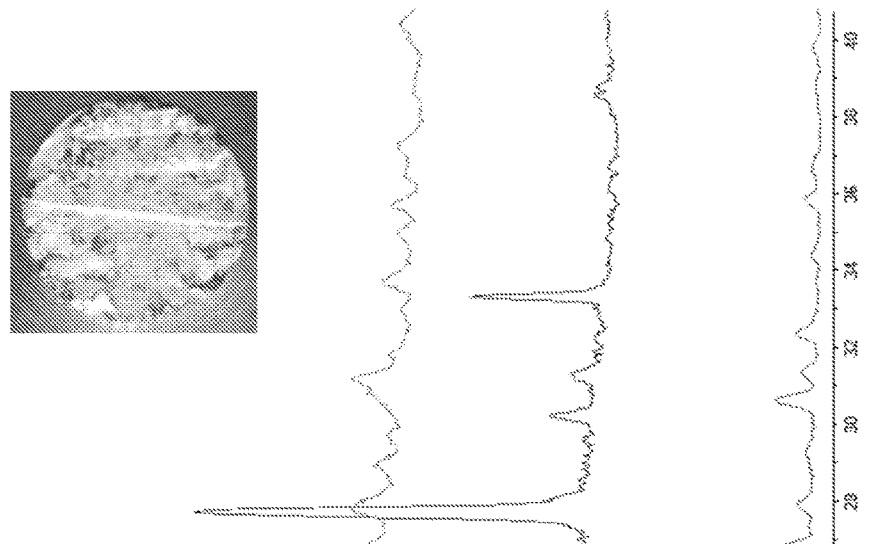

A besylate salt was recovered. FIG. 26A shows XRPD patterns of potential besylate salt Bes1 compared to psilocin free base and benzenesulfonic acid. FIG. 26B shows the vacuum dried besylate salt.

Fumarate salts were recovered. FIG. 27A shows XRPD patterns of the fumarate salts compared to psilocin free base and fumaric acid. Fum1a and Fum1b were obtained as vacuum dry solids. Fum2 and Fum3 were only observed in the wet solids and converted to Fum1b upon drying Fum1a and Fum1b were observed in samples performed with both 1 and 0.5 molar equivalent of fumaric acid, Fum2 and Fum3 were only observed when 0.5 molar equivalent of fumaric acid was used. FIGS. 27B-27E show the different fumarate salts.

Figures 28A, 28B, 28C:
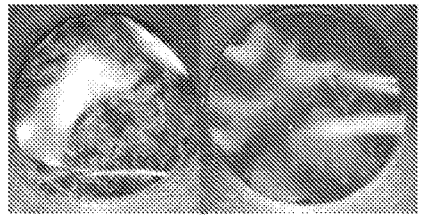
FIG. 28A is a graph of XRPD pattern of glutarate salt (Glt1)
FIG. 28B is a photograph showing the wet glutarate salt.
FIG. 28C is a photograph showing the vacuum dried glutarate salt.

A glutarate salt was recovered. FIG. 28A shows XRPD patterns of glutarate salt Glt1 compared to psilocin free base and glutaric acid. FIG. 28B shows the wet glutarate salt and FIG. 28C shows vacuum dried glutarate salt.

Figure 29B:
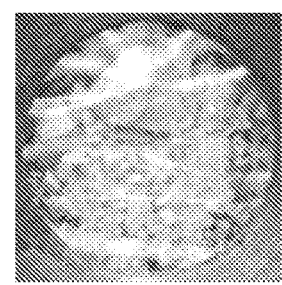
FIG. 29A is a graph of XRPD pattern of lactate salt (Lac1) and FIG. 29B is a photograph showing the vacuum dried lactate salt.
Figure 29A:
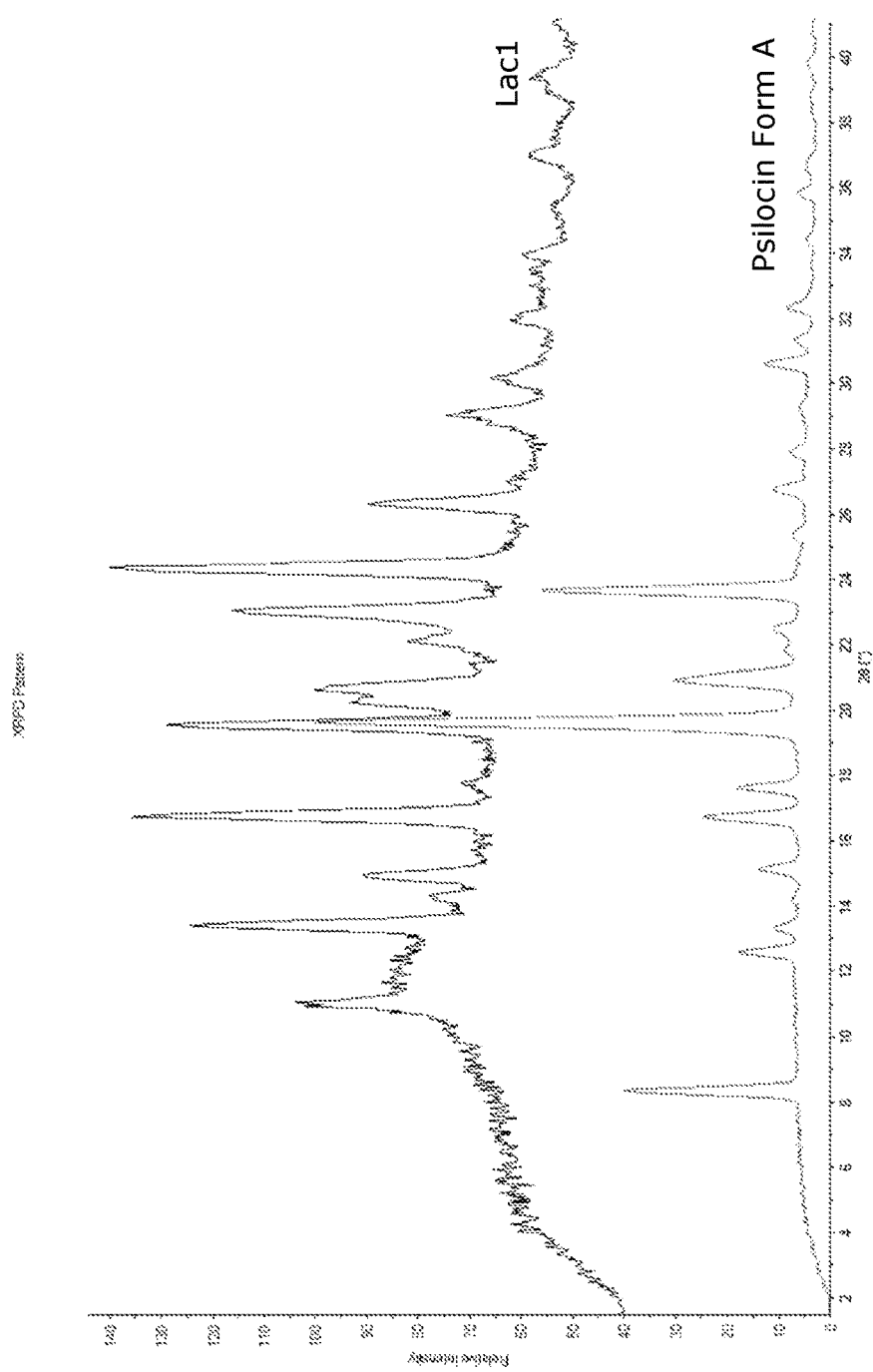

A lactate salt was recovered. FIG. 29A shows XRPD patterns of lactate salt Lac1 compared to psilocin free base and lactic acid. FIG. 29B shows the vacuum dried lactate salt.

Figure 30B:
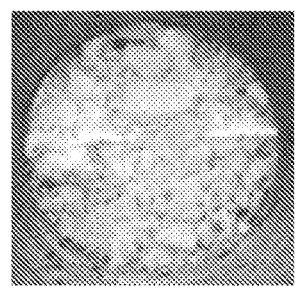
FIG. 30A is a graph of XRPD pattern of malonate salt (Mao1) and FIG. 30B is a photograph showing the vacuum dried malonate salt.
Figure 30A:
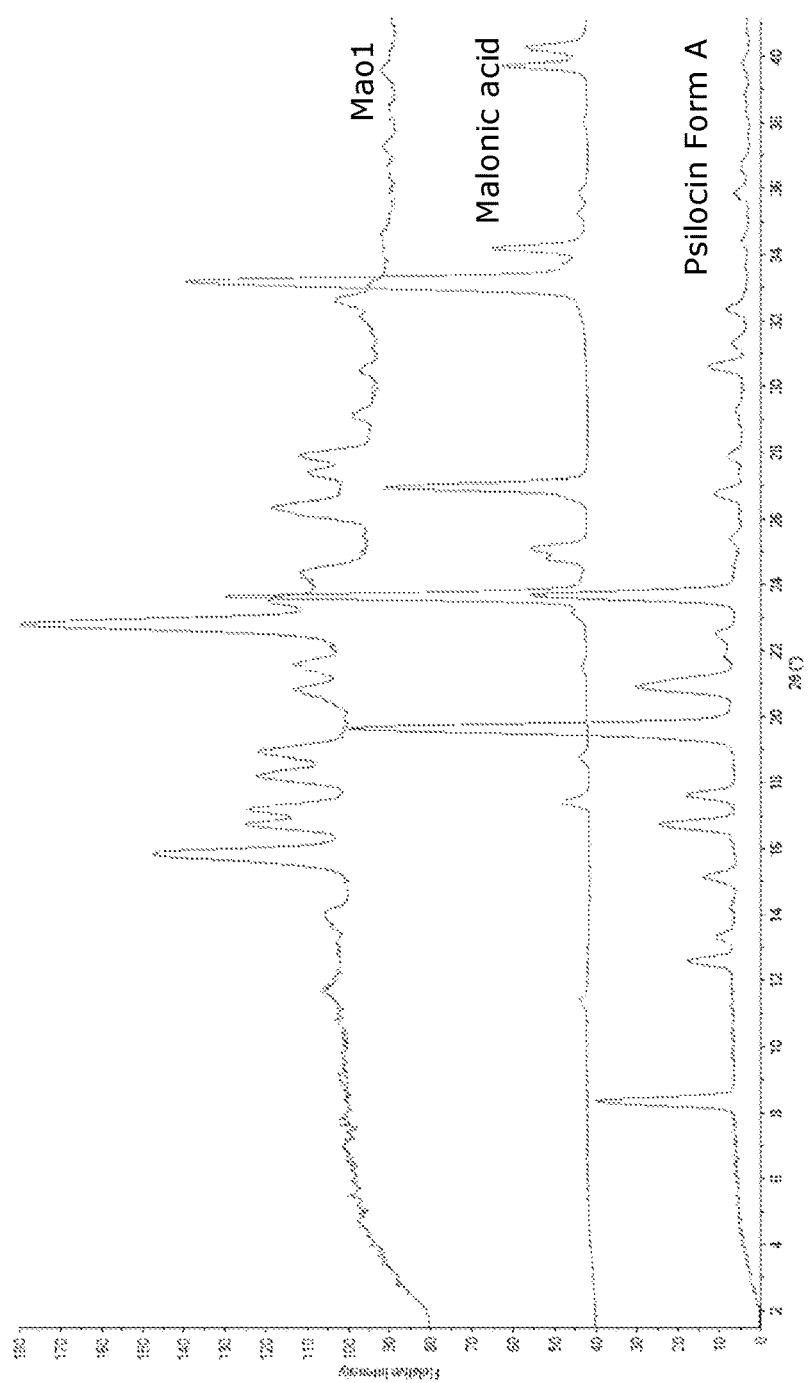

A malonate salt was recovered. FIG. 30A shows XRPD patterns of potential malonate salt Mao1 compared to psilocin free base and malonic acid. FIG. 30B shows the vacuum dried malonate salt.

Oxalate salts were recovered. FIG. 31A shows XRPD patterns of the oxalate salts compared to psilocin free base and oxalic acid. Oxa1a and Oxa1b were obtained from experiments performed with 1 molar equivalent oxalic acid, while the other oxalate salts were obtained from experiments with 0.5 molar equivalent. FIGS. 31B-31G show the different oxalate salts.

Figure 32B:
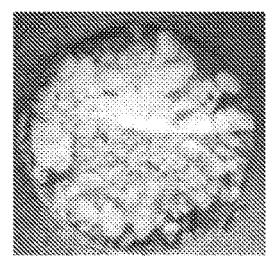
FIG. 32A is a graph of XRPD pattern of phosphate salt (Pho1) and FIG. 32B is a photograph showing the vacuum dried phosphate salt.
Figure 32A:
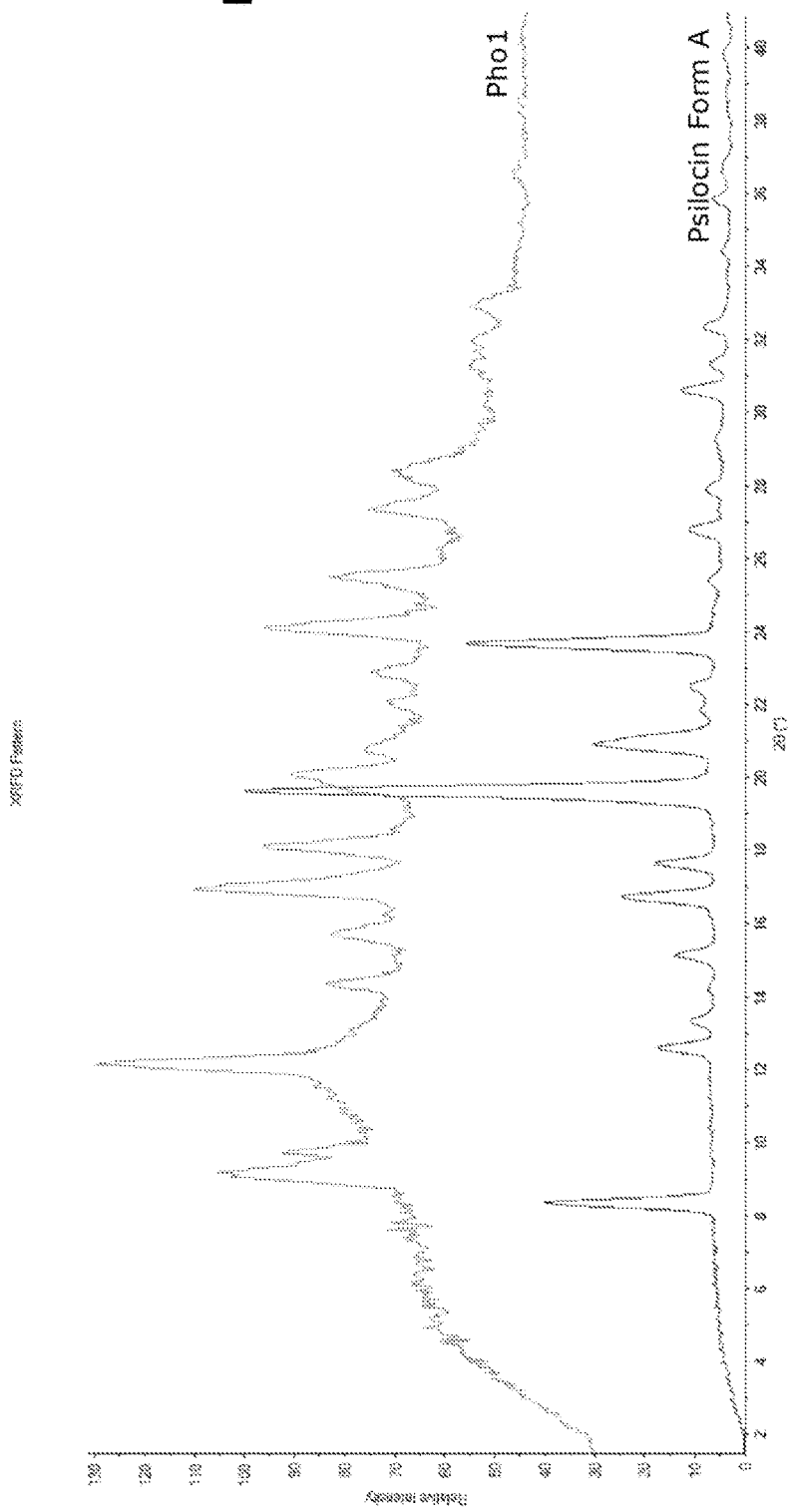

A phosphate salt was recovered. FIG. 32A shows XRPD patterns of phosphate salt Pho1 compared to psilocin free base. FIG. 32B shows the vacuum dried phosphate salt.

Succinate salts were recovered. FIG. 33A shows XRPD patterns of succinate salts compared to psilocin free base and succinic acid. Suc1 was obtained from the experiments performed in MEK (both ratios), and Suc2 was obtained from the experiment performed with 0.5 molar equivalent succinic acid in ACN and converted to Suc3 upon drying. FIGS. 33B-33D show the different succinate salts.

Example 5

Two tartrate forms were identified, Tar1 and Tar2. The thermal stability of the psilocin tartrate salt was evaluated in four solvent systems: water, water/ACN 50/50, Water/THF 50/50 and water/1,4-dioxane 50/50. Solutions of API and tartaric acid were prepared in the selected solvents. These solutions were measured by UPLC-MS and re-measured after storage at 5° C. overnight. The results indicated that the API remains stable in water and 50% water solutions in presence of 1 molar equivalent of tartaric acid.

TABLE 6

| Solvent | Temp., time (° C., h) | RT (min) | Area (mAu*s) | Purity Area (%) |
|---|---|---|---|---|
| Water | RT, t0 | 1.32 | 2513.54 | 99.1 |
| Water | 5° C., 18 h | 1.32 | 2555.19 | 99.0 |
| Water/Acetonitrile 50/50 | RT, t0 | 1.33 | 2102.77 | 99.0 |
| Water/Acetonitrile 50/50 | 5° C., 18 h | 1.33 | 2109.21 | 99.0 |
| Water/THF 50/50 | RT, t0 | 1.32 | 2581.10 | 99.1 |
| Water/THF 50/50 | 5° C., 18 h | 1.30 | 4312.55 | 99.0 |
| Water/1,4-Dioxane 50/50 | RT, t0 | 1.32 | 2335.92 | 98.9 |
| Water/1,4-Dioxane 50/50 | 5° C., 18 h | 1.25 | 10262.35 | 99.0 |

Freeze Drying Tartrate Salt Solutions.

Figure 34:
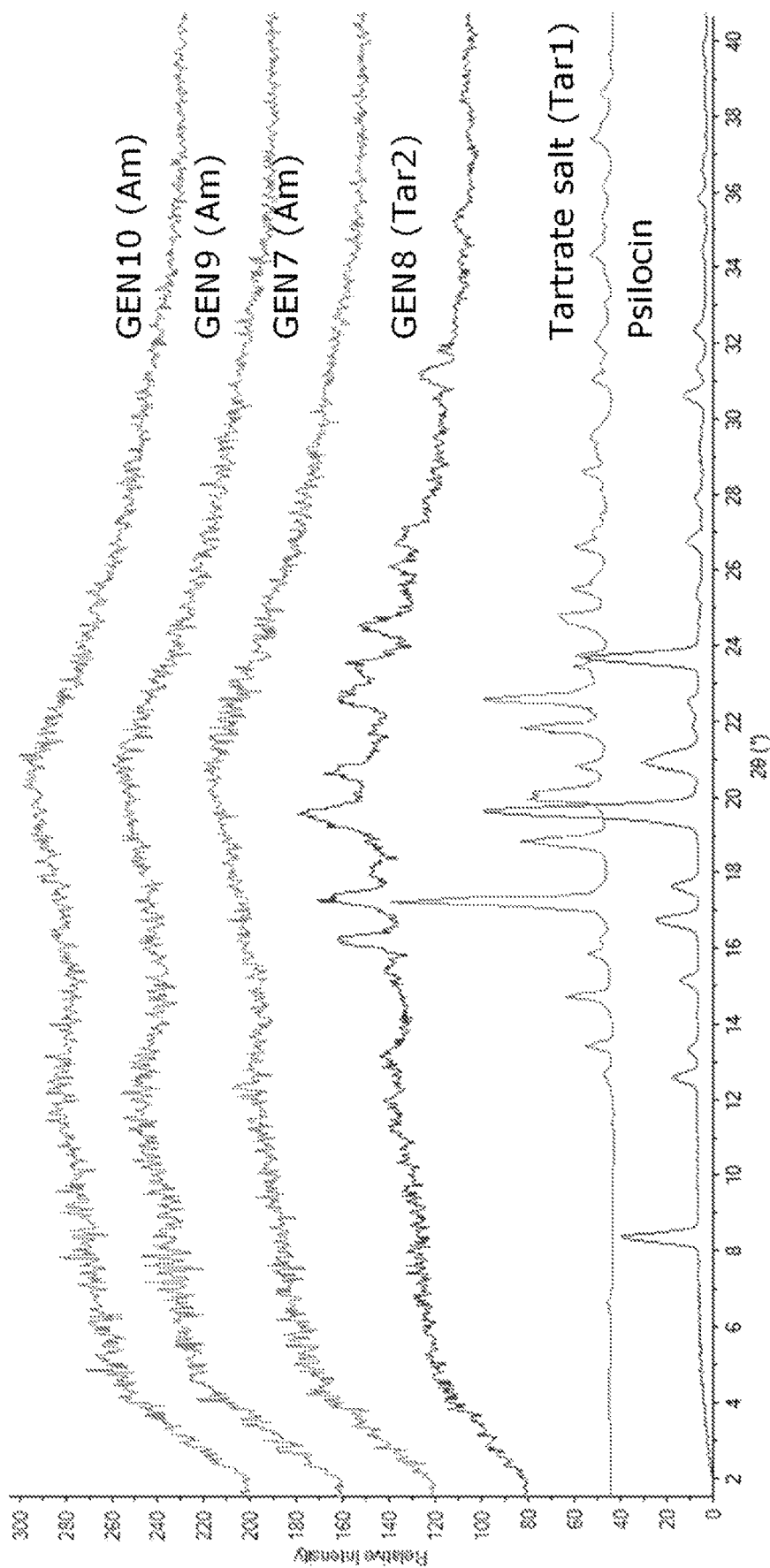
FIG. 34 is a graph of XRD patterns for psilocin free base, psilocin tartrate salt Form 1 (Tar1), psilocin tartrate salt Form 2 (Tar2) and three examples of amorphous psilocin tartrate salt (Am)

FIG. 34 shows a comparison of the XRD patterns for psilocin free base, psilocin tartrate salt Form 1 (Tar1), psilocin tartrate salt Form 2 (Tar2) and three examples of amorphous psilocin tartrate salt (Am). 20 mg of API and 15 mg of tartaric acid were weighed in vials (molar ratio 1:1). Aliquots of 100 µL solvent were added until the solids were dissolved. The obtained solutions were frozen in liquid nitrogen and placed in the freeze-dryer overnight. From water, water/THF 50/50 and water/dioxane 50/50 amorphous solids were recovered. The solid from water contained 1.3% residual water, while the solids obtained from the THF and dioxane mixtures contained 7.8 and 10.3% solvent, respectively. The solid obtained from the acetonitrile mixture was crystalline and had a different XRPD than the free base or the already known tartrate salt and was designated Tar2. All solids had a purity of about 99%. The material to be used for polymorph screening was prepared by freeze drying a solution in water.

Thermocycling Tartrate Salt.

Figure 35:
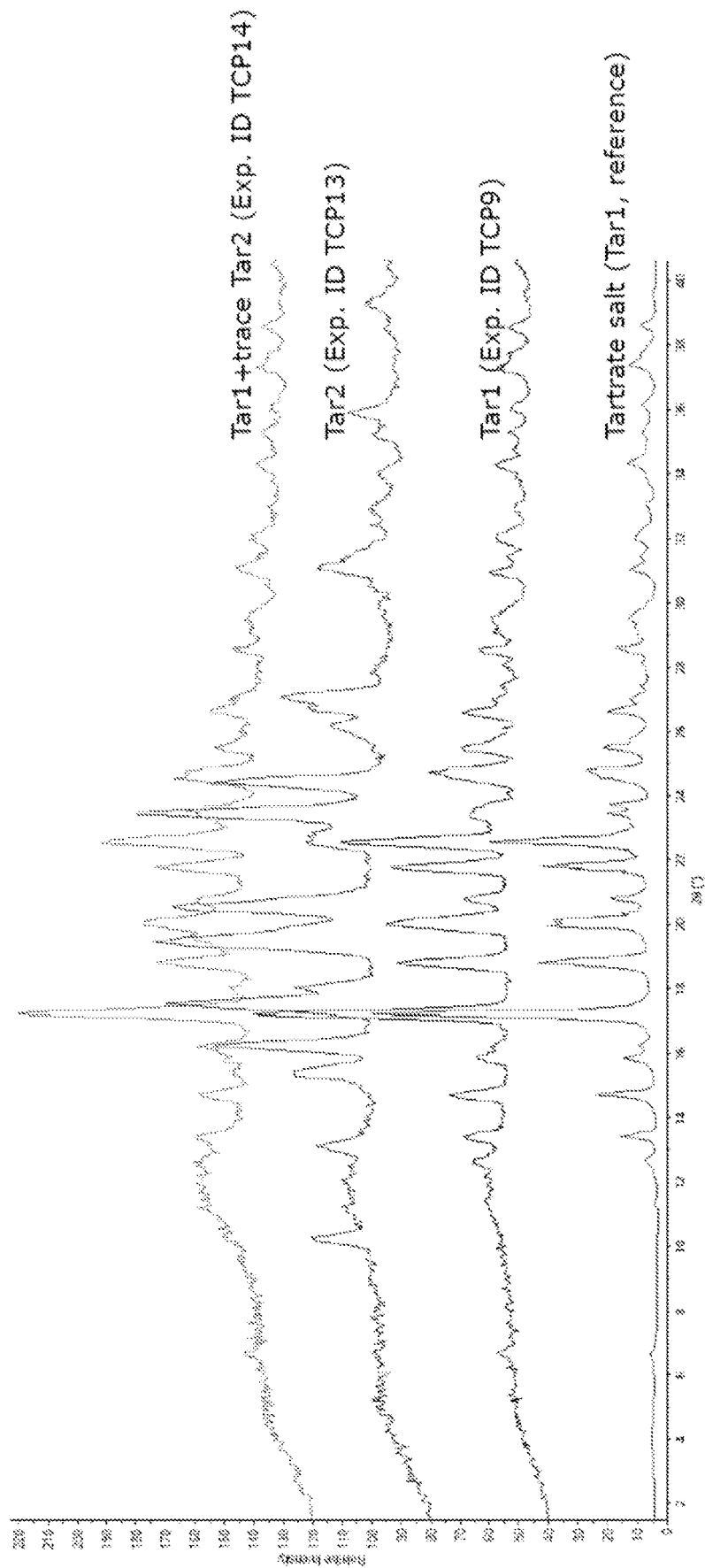
FIG. 35 is an overlay comparing the XRPD pattern of psilocin tartrate salt Form 1 (Tar1) and Form 2 (Tar2)

FIG. 35 is an overlay comparing the XRPD pattern of psilocin tartrate salt Form 1 (Tar1) and Form 2 (Tar2). TCP13 was isolated from acetone/water, 95:5 as follows. To about 35 mg of amorphous psilocin tartrate salt, acetone/water (95:5) was added in small aliquots until a thin suspension was obtained. The suspension was subjected to a temperature cycling profile, of 3 cycles between 5 and 50° C. with a heating rate of 10° C./h and cooling rates of 20, 10 and 5° C./h, with a final aging stage at 25° C. for 48 hours. The solids were isolated and analyzed by XRPD after drying at ambient conditions and under vacuum at 50 C. The gently dried and harshly dried solids had the same XRPD patterns.

TABLE 7 shows high throughput XRPD peak information for Tar1 and TABLE 8 shows high throughput XRPD peak information for Tar2. XRPD peak information from high resolution XRPD may vary from that presented in these tables.

TABLE 7

| Peak ID | Angle (2θ) | d-Spacing | Intensity |
|---|---|---|---|
| 1 | 13.42 | 6.59 | 28.9 |
| 2 | 14.7 | 6.02 | 33.71 |
| 3 | 17.22 | 5.14 | 100 |
| 4 | 18.78 | 4.72 | 51.09 |
| 5 | 20.02 | 4.43 | 55.4 |
| 6 | 20.82 | 4.26 | 28.38 |
| 7 | 21.78 | 4.08 | 53.7 |
| 8 | 22.54 | 3.94 | 69.37 |
| 9 | 24.7 | 3.6 | 37.17 |
| 10 | 25.46 | 3.49 | 29.16 |
| 11 | 26.58 | 3.35 | 28.75 |
| 12 | 28.5 | 3.13 | 23.05 |
| 13 | 30.94 | 2.89 | 20.16 |

TABLE 8

| Peak ID | Angle (2θ) | d-Spacing | Intensity |
|---|---|---|---|
| 1 | 10.22 | 8.65 | 39.16 |
| 2 | 13.1 | 6.75 | 38.3 |
| 3 | 15.38 | 5.75 | 46.83 |
| 4 | 16.26 | 5.44 | 72.52 |
| 5 | 17.54 | 5.05 | 89.84 |
| 6 | 18.02 | 4.92 | 46.48 |
| 7 | 19.46 | 4.56 | 94.32 |
| 8 | 20.54 | 4.32 | 87.82 |
| 9 | 23.46 | 3.79 | 99.98 |
| 10 | 24.46 | 3.63 | 70.26 |
| 11 | 26.14 | 3.4 | 33.91 |
| 12 | 27.06 | 3.29 | 51 |
| 13 | 31.1 | 2.87 | 37.28 |
| 14 | 35.9 | 2.5 | 27.97 |

Figure 36A:
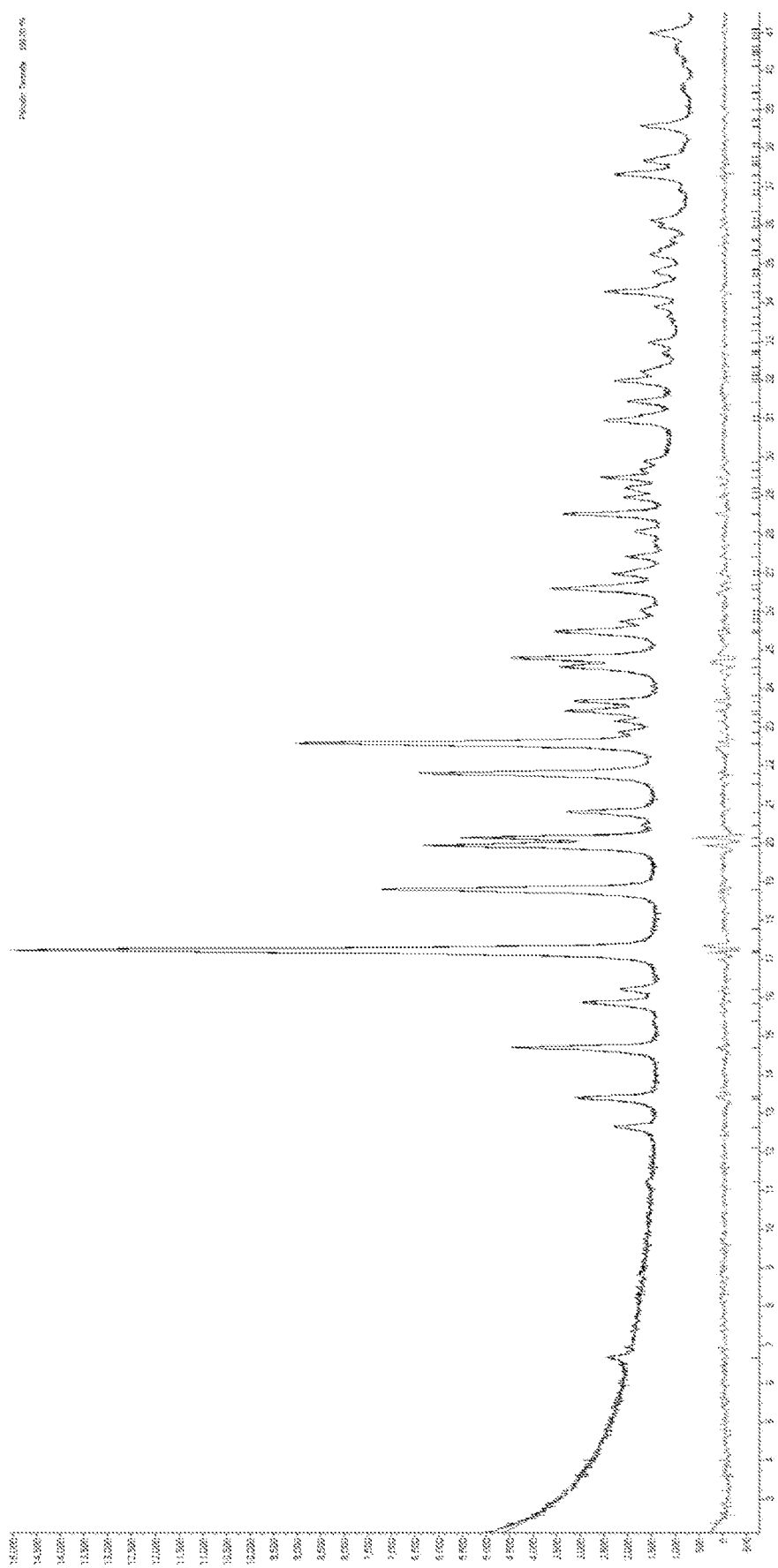
FIG. 36A is an XPRD graph of Tar1.

FIG. 36A shows an XPRD graph of Whole Powder Pattern Decomposition analysis of the tartrate salt Tar1. The refinement data and cell parameters are shown in TABLE 9.

TABLE 9

| Experiment ID | TCP11 |
|---|---|
| Polymorph | Psilocin Tartrate |
| Empirical formula | C12H17N2O+ C4H5O6− |
| Formula weight | 354.36 |
| T [K] | 296 |
| lambda[Å] | 1.54056 |

TABLE 9-continued

| Crystal system | Orthorhombic |
|---|---|
| Proposed space group | P212121 |
| Unit cell dimensions | |
| a[Å] | 7.5944(9) |
| b[Å] | 8.2458(9) |
| c[Å] | 26.4419(18) |
| V[Å$^3$] | 1655.8(3) |
| Z (Z') | 4(1) |
| Dc [g/cm$^3$] | 1.421 |
| Cap. size [mm2] | 0.3 × 8 |
| 2theta Step size [°] | 0.0157 |
| No of steps | 2500 |
| Time per step [s] | 10 |
| 2theta range [°] | 2.15-41.5 |
| Rexp | 2.32 |
| Rwp | 3.26 |
| Rp | 2.54 |
| GOF | 1.40 |
| RBrag | 0.16 |
| Impurities, other forms [%] | Below detection limits |

Figure 36B:
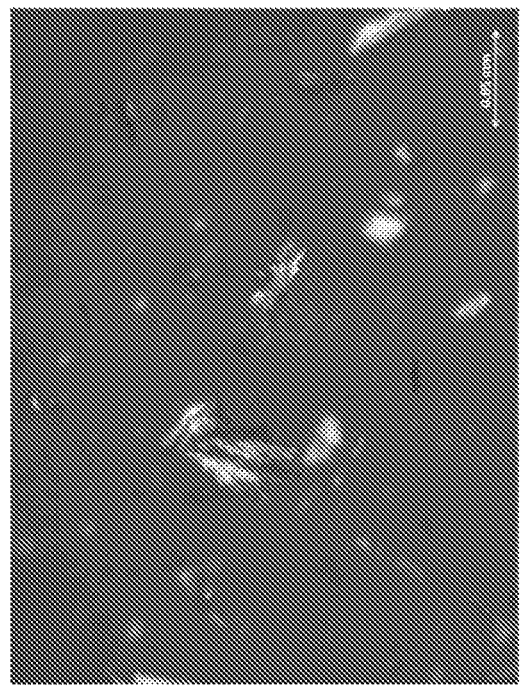
FIG. 36B is a polarized light microscopy image of crystals of Tar1.

FIG. 36B shows the polarized light microscopy image taken with 20× magnification. The solid consists of small needle like crystals with longest size close to 0.05 mm that are arranged in aggregates looking like hay sheaves.

XPRD peak data is shown in TABLE 10.

TABLE 10

| Peak ID | Angle (2θ) | d-Spacing | Intensity |
|---|---|---|---|
| 1 | 6.67 | 13.24 | 3 |
| 2 | 11.22 | 7.88 | 1 |
| 3 | 12.64 | 7.00 | 6 |
| 4 | 13.40 | 6.60 | 13 |
| 5 | 14.71 | 6.02 | 23 |
| 6 | 15.86 | 5.58 | 12 |
| 7 | 16.20 | 5.47 | 6 |
| 8 | 17.23 | 5.14 | 100 |
| 9 | 18.80 | 4.72 | 43 |
| 10 | 19.94 | 4.45 | 36 |
| 11 | 20.15 | 4.40 | 31 |
| 12 | 20.81 | 4.27 | 14 |
| 13 | 21.82 | 4.07 | 37 |
| 14 | 22.58 | 3.93 | 57 |
| 15 | 22.86 | 3.89 | 6 |
| 16 | 23.15 | 3.84 | 6 |
| 17 | 23.41 | 3.80 | 14 |
| 18 | 23.67 | 3.76 | 13 |
| 19 | 24.57 | 3.62 | 14 |
| 20 | 24.78 | 3.59 | 21 |
| 21 | 25.48 | 3.49 | 16 |
| 22 | 25.73 | 3.46 | 6 |
| 23 | 26.02 | 3.42 | 3 |
| 24 | 26.60 | 3.35 | 16 |

Figure 37A:
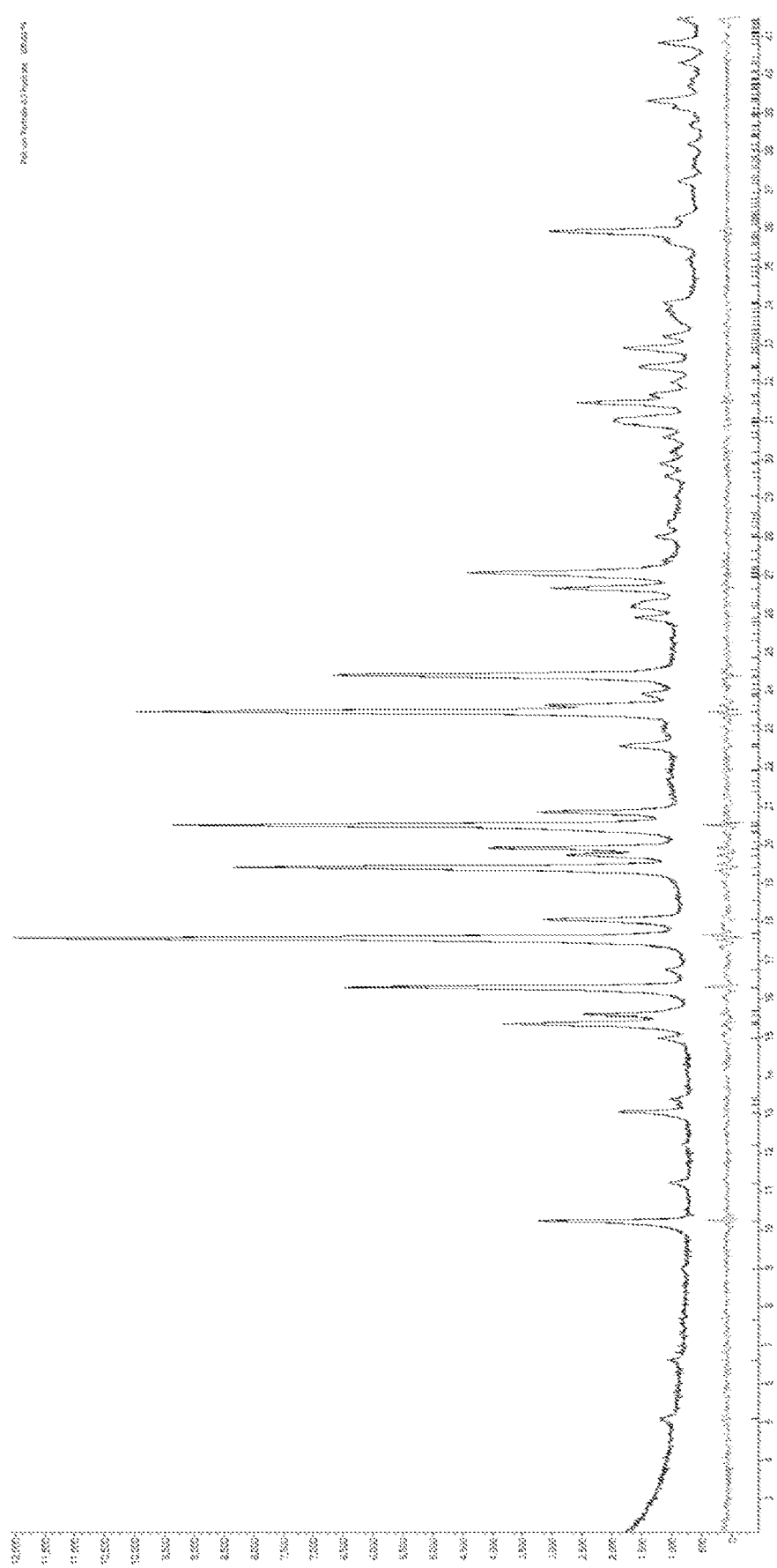
FIG. 37A is an XPRD graph of Tar2.

FIG. 37A shows an XPRD graph of Whole Powder Pattern Decomposition analysis of the tartrate salt Tar2. The refinement data and cell parameters are shown in TABLE 11.

TABLE 11

| Experiment ID | TCP12 |
|---|---|
| Polymorph | Psilocin Tartrate 0.3 hydrate |
| Empirical formula | C$_{12}$H$_{17}$N$_2$O$^+$ C$_4$H$_5$O$_6^-$ 0.3 H$_2$O |
| Formula weight | 359.76 |
| T [K] | 296 |
| lambda[Å] | 1.54056 |
| Crystal system | Monoclinic |
| Proposed space group | C2 |
| Unit cell dimensions | |
| a[Å] | 27.0989(21) |
| b[Å] | 7.5302(3) |
| c[Å] | 17.5540(12) |

TABLE 11-continued

| | |
|---|---|
| V[Å³] | 99.516(3) |
| Z (Z') | 3532.8(4) |
| Dc [g/cm³] | 8(2) |
| Cap. size [mm2] | 1.353 |
| 2theta Step size [°] | 0.7 × 8 |
| No of steps | 0.0157 |
| Time per step [s] | 2500 |
| 2theta range [°] | 5 |
| Rexp | 2.15-41.5 |
| Rwp | 2.92 |
| Rp | 3.62 |
| GOF | 2.78 |
| RBrag | 1.24 |
| Impurities, other forms [%] | 0.31 |

Figure 37B:
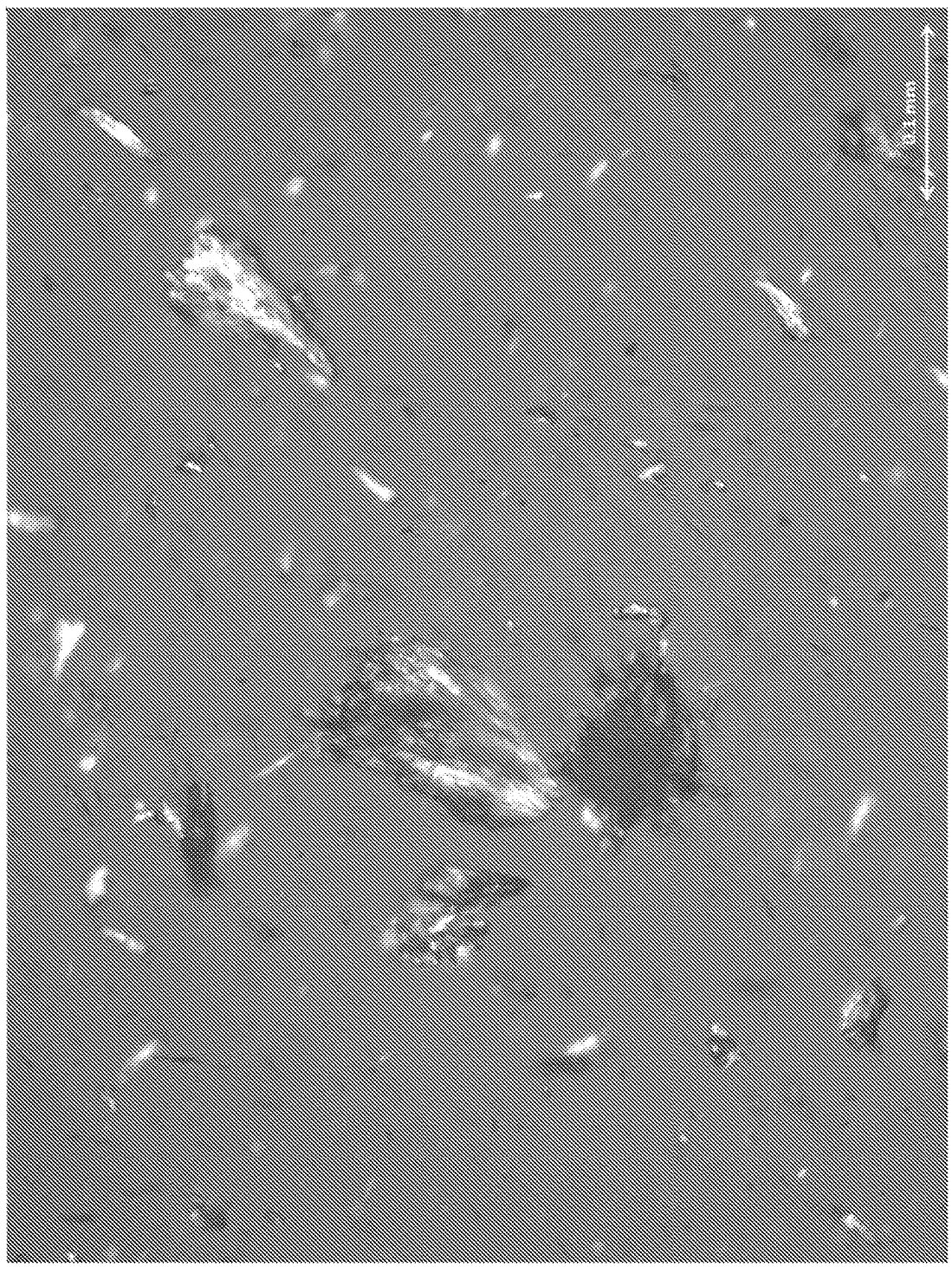
FIG. 37B is a polarized light microscopy image of crystals of Tar2.

FIG. 37B shows the polarized light microscopy image taken with 10× magnification. The solid consists of small needle like crystals with longest size close to 0.05 mm that are arranged in aggregates looking like hay sheaves.

XPRD peak data are shown in TABLE 12.

TABLE 12

| Peak ID | Angle (2θ) | d-Spacing | Intensity |
|---|---|---|---|
| 1 | 5.08 | 17.37 | 2 |
| 2 | 6.61 | 13.36 | 2 |
| 3 | 9.02 | 9.80 | 1 |
| 4 | 10.21 | 8.65 | 23 |
| 5 | 11.22 | 7.88 | 3 |
| 6 | 13.07 | 6.77 | 11 |
| 7 | 13.41 | 6.60 | 3 |
| 8 | 14.97 | 5.91 | 4 |
| 9 | 15.36 | 5.76 | 28 |
| 10 | 15.59 | 5.68 | 15 |
| 11 | 16.29 | 5.44 | 51 |
| 12 | 16.74 | 5.29 | 2 |
| 13 | 17.57 | 5.04 | 100 |
| 14 | 18.05 | 4.91 | 20 |
| 15 | 19.41 | 4.57 | 67 |
| 16 | 19.73 | 4.50 | 17 |
| 17 | 19.92 | 4.45 | 29 |
| 18 | 20.51 | 4.33 | 76 |
| 19 | 20.85 | 4.26 | 21 |
| 20 | 22.57 | 3.94 | 8 |
| 21 | 23.45 | 3.79 | 81 |
| 22 | 23.65 | 3.76 | 18 |
| 23 | 23.90 | 3.72 | 5 |
| 24 | 24.40 | 3.65 | 52 |

Example 6

HR-XPRD of Psilocin Form A.

Figure 38A:
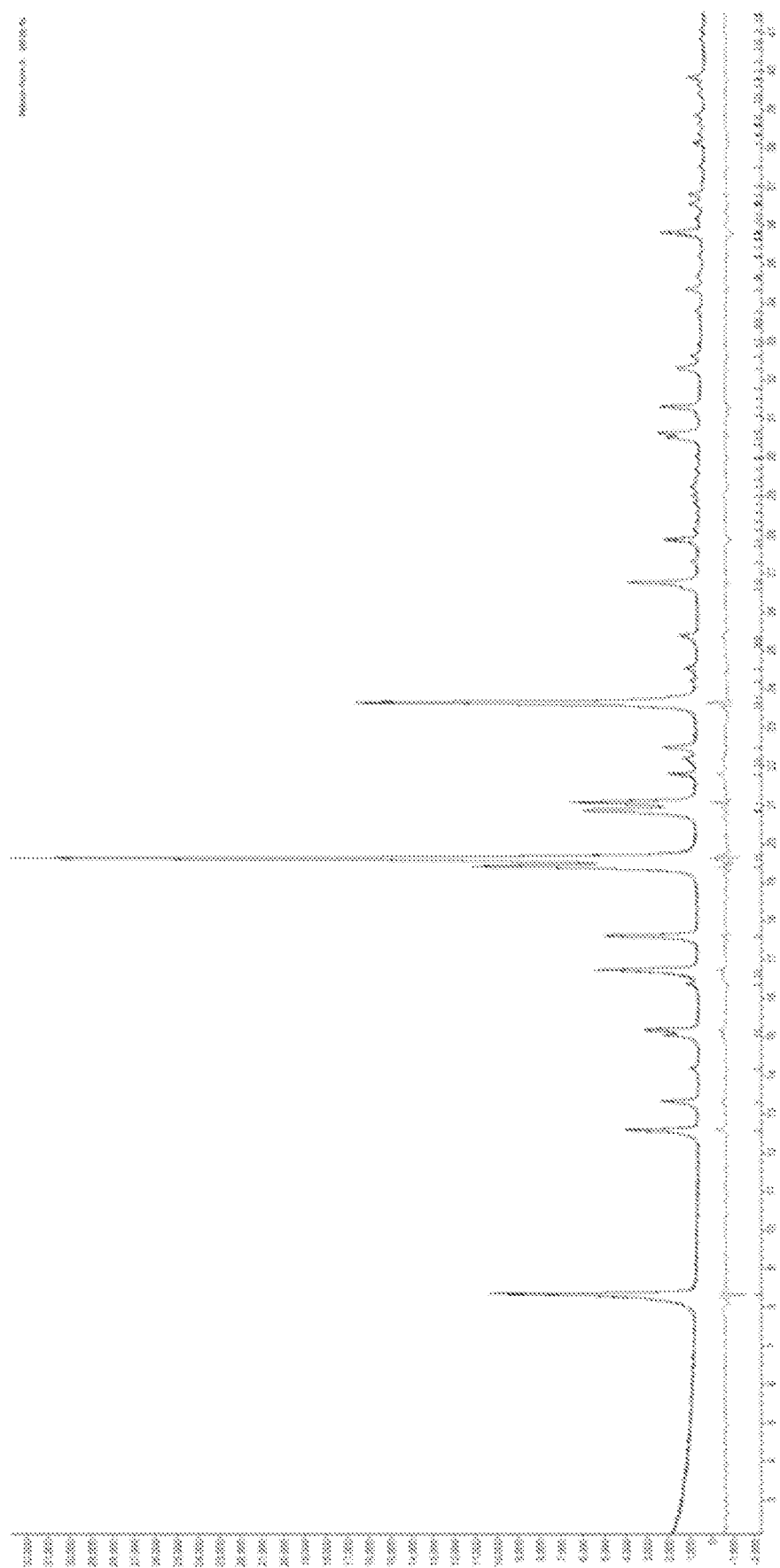
FIG. 38A is an XPRD graph of psilocin form A.

Rietveld analysis of psilocin as received, using CCDC 1238288 single crystal data as a model is shown in FIG. 38A.

The experimental conditions and cell parameters are shown in TABLE 13.

TABLE 13

| Compound | Psilocin |
|---|---|
| Polymorph | Form A |
| Empirical formula | C₁₂H₁₆N₂O |
| Formula weight | 204.27 |
| T [K] | 296(2) K |
| lambda[Å] | 1.54056 |
| Crystal system | Monoclinic |
| Space group | P21/c |
| Cap. size [mm2] | 0.5 × 8 |
| 2theta Step size [°] | 0.016 |
| No of steps | 2503 |
| Time per step [s] | 15 |

TABLE 13-continued

| | |
|---|---|
| 2theta range [°] | 2.15→ 41.5 |
| Rexp | 3.05 |
| Rwp | 5.31 |
| Rp | 4.01 |
| GOF | 1.74 |
| RBrag | 2.05 |
| Impurities, other forms [%] | Below Detection Limits |

Figure 38B:
FIG. 38B is a polarized light microscopy image of crystals of psilocin form A.

FIG. 38B shows the polarized light microscopy image taken with 20× magnification. The solid consists of plate like crystals with the longest sizes close to 0.05 mm.

XPRD peak values are shown in TABLE 14.

TABLE 14

Peak table for Psilocin Form A

| Peak ID | Angle (2θ) | d-Spacing | Intensity |
|---|---|---|---|
| 1 | 8.35 | 10.58 | 29 |
| 2 | 12.59 | 7.02 | 11 |
| 3 | 13.34 | 6.63 | 6 |
| 4 | 14.21 | 6.23 | 1 |
| 5 | 15.06 | 5.88 | 5 |
| 6 | 15.18 | 5.83 | 8 |
| 7 | 16.38 | 5.41 | 1 |
| 8 | 16.73 | 5.30 | 15 |
| 9 | 17.63 | 5.03 | 13 |
| 10 | 19.42 | 4.57 | 33 |
| 11 | 19.62 | 4.52 | 100 |
| 12 | 20.87 | 4.25 | 16 |
| 13 | 21.08 | 4.21 | 18 |
| 14 | 21.81 | 4.07 | 4 |
| 15 | 22.19 | 4.00 | 2 |
| 16 | 22.50 | 3.95 | 5 |
| 17 | 23.65 | 3.76 | 50 |
| 18 | 24.23 | 3.67 | 1 |
| 19 | 24.55 | 3.62 | 1 |
| 20 | 25.39 | 3.51 | 3 |
| 21 | 26.77 | 3.33 | 10 |

Example 7

Figure 39:
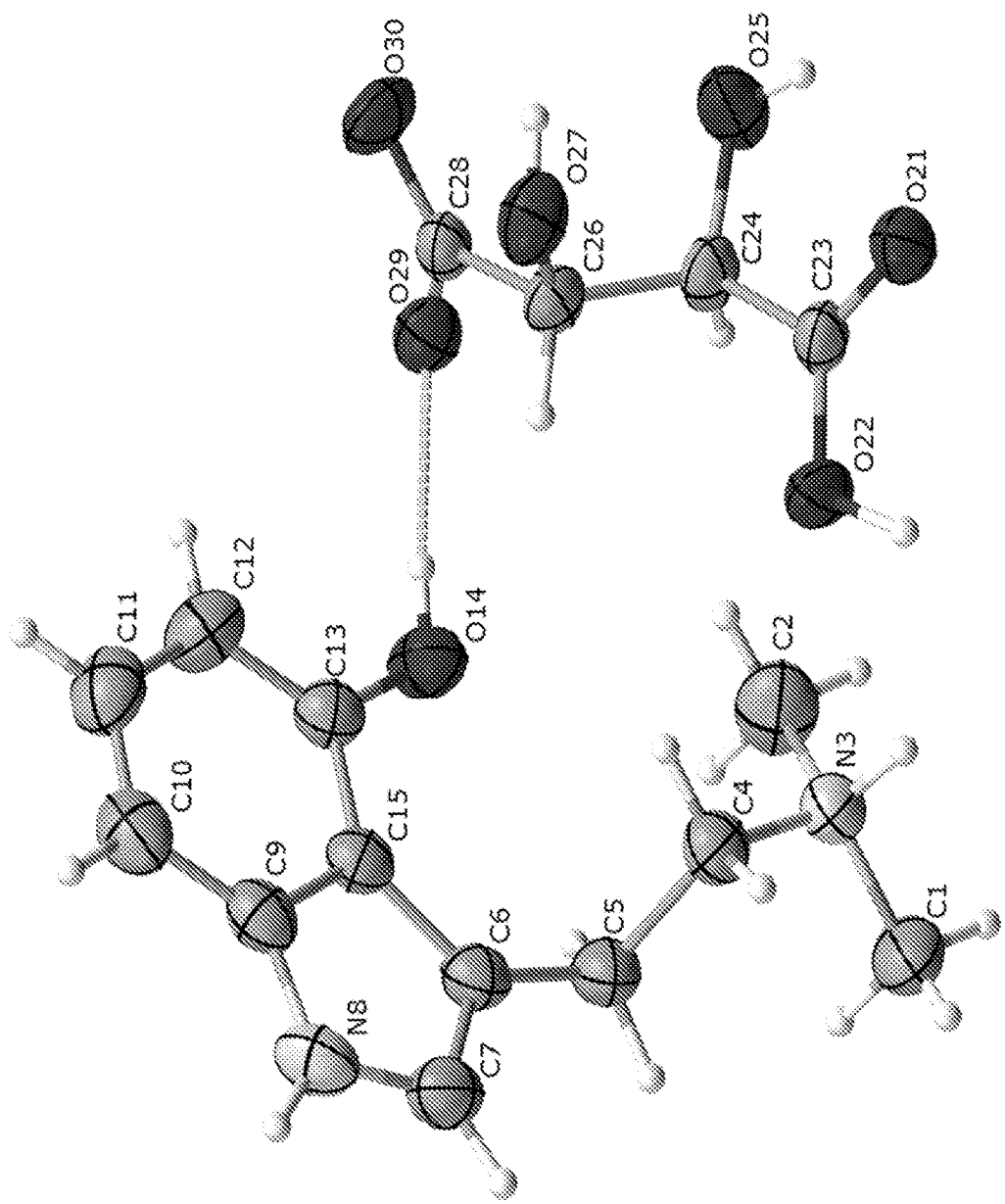
FIG. 39 is a representation of an asymmetric unit of psilocin tartrate crystal (Tar1)

FIG. 39 shows an asymmetric unit of psilocin tartrate crystal (Tar1), with the hydrogen bond shown between the two molecules. The charged N3 atom interacts in bifurcated hydrogen bonds. One interaction is directed toward the carboxylic non deprotonated acidic group, while the second interaction is directed toward the (deprotonated) acidic carboxylate group. The N—H group from the fused ring act as H-bond donor to the hydroxyl group of the anion closer to the carboxylate (O27) as acceptor. The crystal is built up by an extensive hydrogen bonds network, where each N or O connected H atom is utilized as donor of hydrogen bonds, while every O atom serves as hydrogen bonds acceptor. TABLE 15 shows crystallographic parameters.

TABLE 15

| Form | Psylocin tartrate (Tar1) |
|---|---|
| Empirical formula | C₁₆H₂₂N₂O⁺ C₄H₅O₆⁻ |
| Formula weight | 354.35 |
| T [K] | 296(2) K |
| λ [Å] | 0.71073 Å |
| Crystal system | Orthorhombic |
| Space group | P2₁2₁2₁ |
| Unit cell dimensions | |
| a [Å] | 26.4225(9) |
| b [Å] | 7.5909(4) |
| c [Å] | 8.2544(3) |

TABLE 15-continued

| | |
|---|---|
| β [°] | — |
| V[Å$^3$] | 1655.59(12) |
| Z(z') | 4 |
| Dc [g/cm$^3$] | 1.422 |
| μ [mm−1] | 0.112 |
| F(000) | 752 |
| Crystal size [mm3] | 0.45 × 0.28 × 0.02 |
| θ range for data collection [°] | 2.6 → 32.6 |
| Reflections collected | 12971 |
| Independent reflections | 5664 [R(int) = 0.0462] |
| Completeness to θ = 22.0° [%] | 99.5% |
| Absorption correction | Semi-empirical from equivalents |
| Max. and min. transmission | 0.998 and 0.736 |
| Data/restraints/parameters | 5664/0/251 |
| Goodness-of-fit on F2 | 0.901 |
| Final R indices [I > 2σ(I)] | R1 = 0.0414, wR2 = 0.0900 |
| R indices (all data) | R1 = 0.0795, wR2 = 0.1008 |
| Absolute structure parameter | 1.3(8) |
| Extinction coefficient | n/a |
| Largest diff. peak and hole [e/Å$^3$] | 0.145 and −0.163 |

Figure 40:
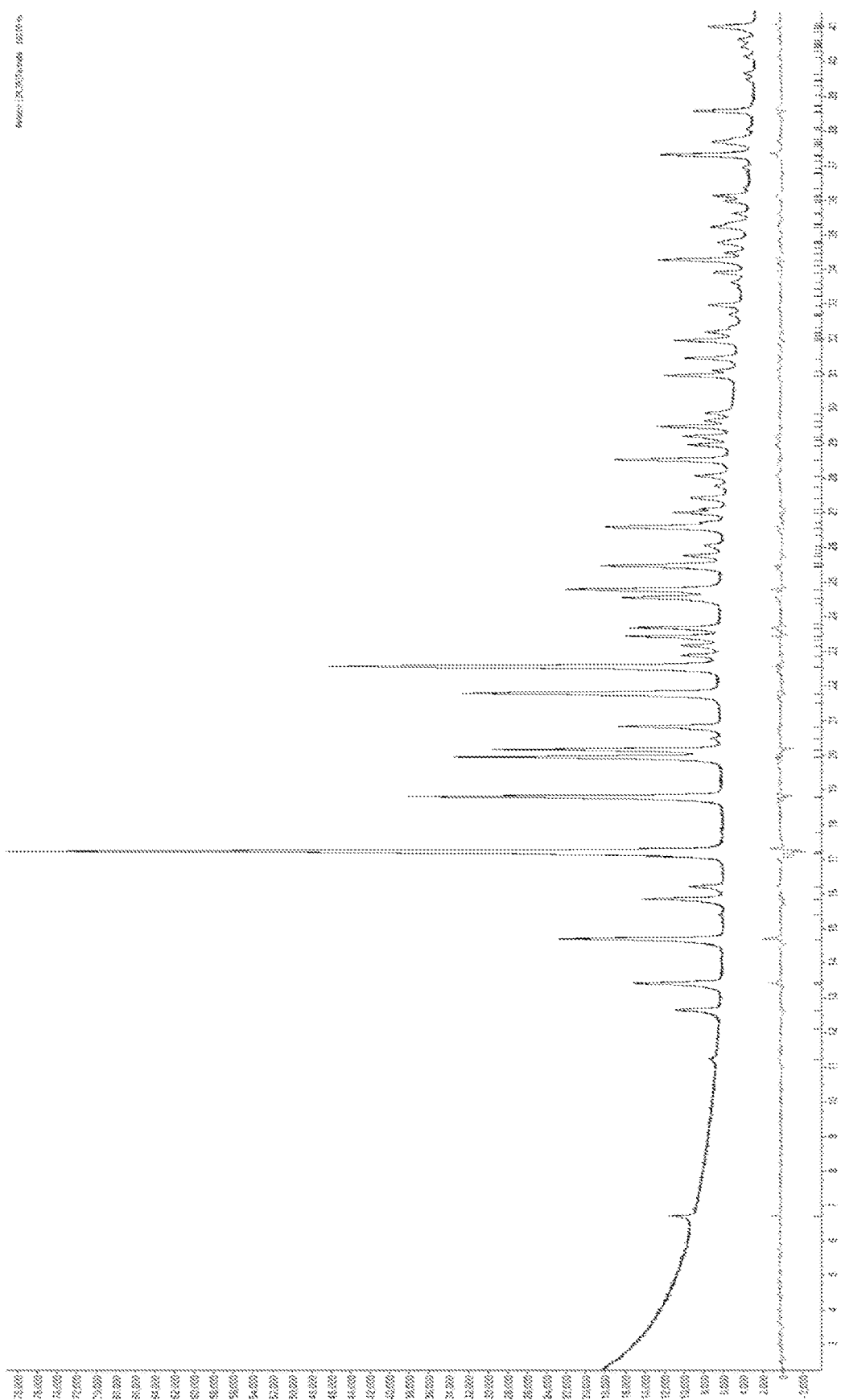
FIG. 40 is a Rietveld analysis on solid obtained by evaporation of a solution of psilocin tartrate Tar1 in ethanol, using the single crystal data of psilocin tartrate as a model.

A HR-XRPD pattern was collected using the crushed crystals that were obtained by evaporation from ethanol. Comparison of this HR-XRPD pattern with the simulated XRPD from the single crystal data confirmed that the patterns were identical. Rietveld analysis was performed on the HR-XRPD data, using the single crystal data as model. No crystalline impurities were detected (FIG. 40, TABLE 16). The top lines represent collected data and calculated and the bottom line is the difference between them. The sticks at the bottom show the peak positions of the unit cell.

TABLE 16

| | |
|---|---|
| Form | Psilocin Tartrate Monohydrate |
| Empirical formula | C$_{16}$H$_{22}$N$_2$O$^+$ C$_4$H$_5$O$_6^-$ |
| Formula weight | 354.35 |
| T [K] | 296 |
| λ[Å] | 1.54056 |
| Crystal system | Orthorhombic |
| Space group | P2$_1$2$_1$2$_1$ |
| Cap. size [mm2] | 0.5 × 8 |
| 2θ Step size [°] | 0.016 |
| No of steps | 2499 |
| Time per step [s] | 5 |
| 2θ range [°] | 2.15.41.5 |
| Rexp | 1.13 |
| Rwp | 2.20 |
| Rp | 1.60 |
| GOF | 1.94 |
| RBrag | 1.46 |
| Impurities, other forms [%] | Below detection limit |

Example 8

Hydrobromide Salt, HBr1

Figures 41A, 41B:
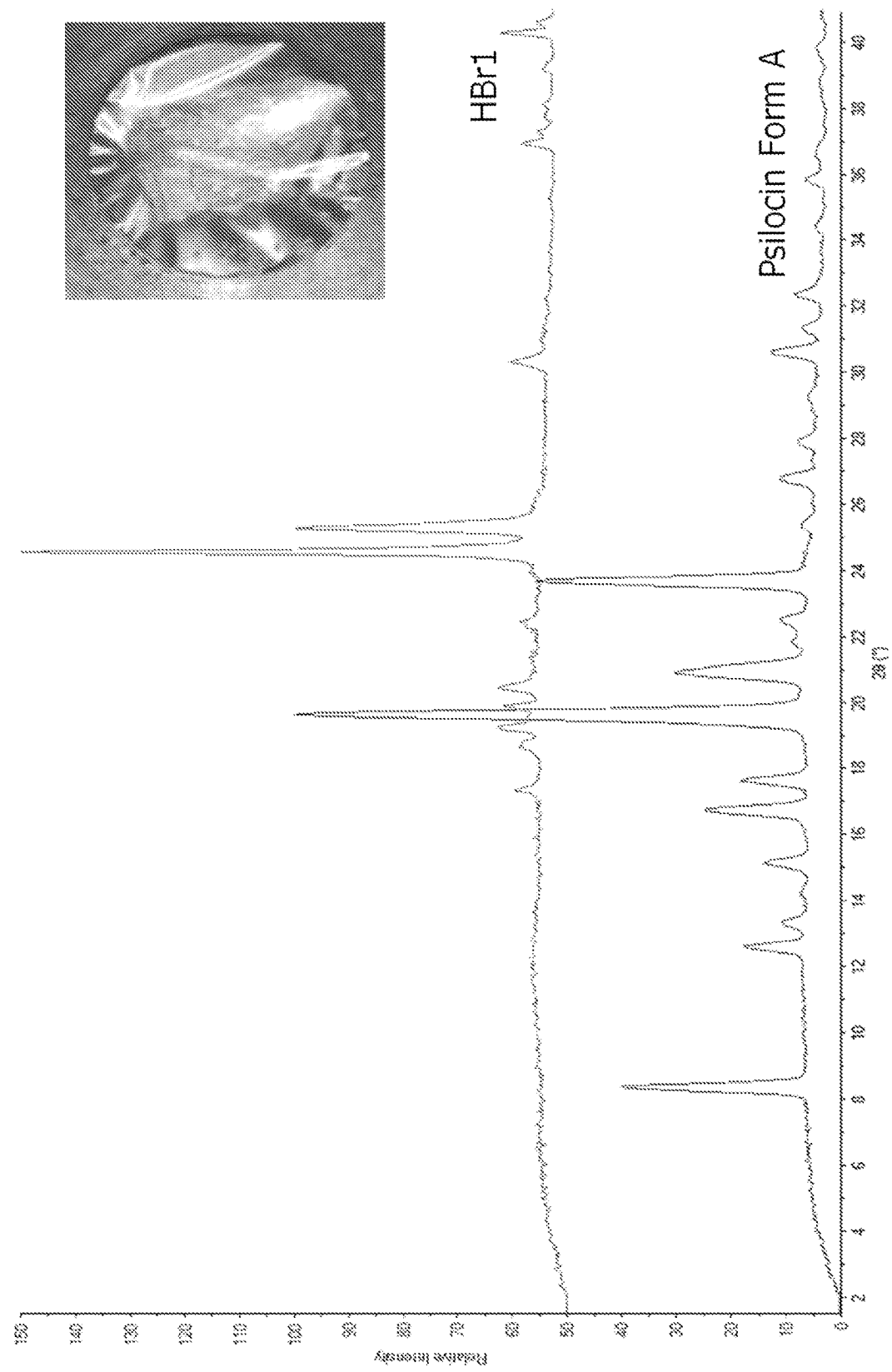
FIG. 41A is a HT-XPRD pattern of psilocin (bottom) and HBr1 (top)
FIG. 41B is an image of the material of HBr1.

Evaporation of the mother liquor of a salt screen experiment performed with 1.1 molar equivalent of hydrobromic acid in MEK resulted in the recovery of HBr1. The HT-XRPD pattern of the solid are shown in FIG. 41A. HBr1 was unstable upon exposure to AAC for two days and became deliquescent. FIG. 41B shows an image of the material of HBr1.

Figure 42:
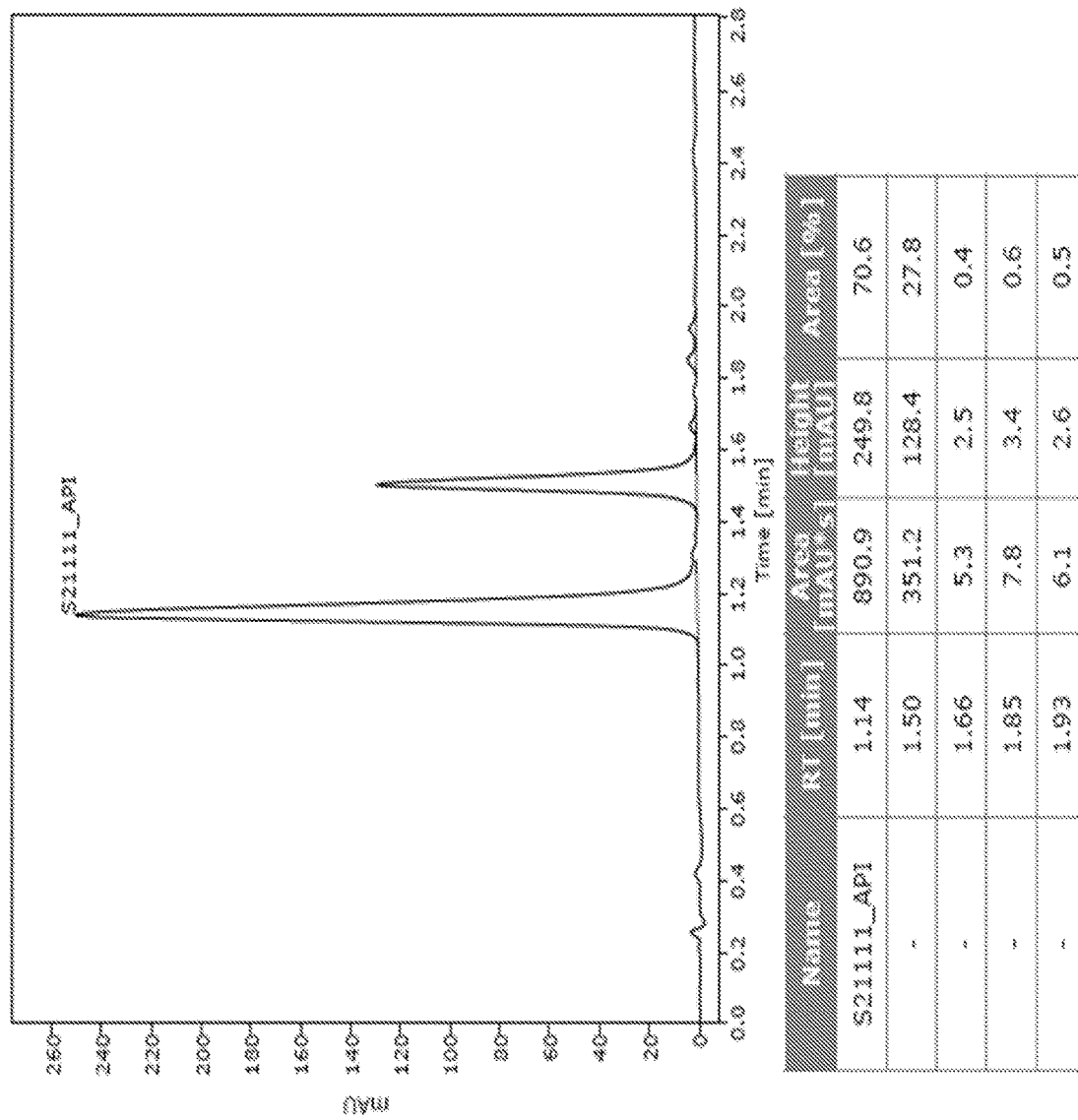
FIG. 42 is a UPLC chromatogram of HBr1.

The UPLC analysis of HBr1 (FIG. 42) showed the presence of the API peak with the chemical purity of 70.6% (area %). The peak at 1.5 min corresponded to a m/z of 277 (M+72)$^+$, possibly due to a reaction of API with MEK.

Figure 43:
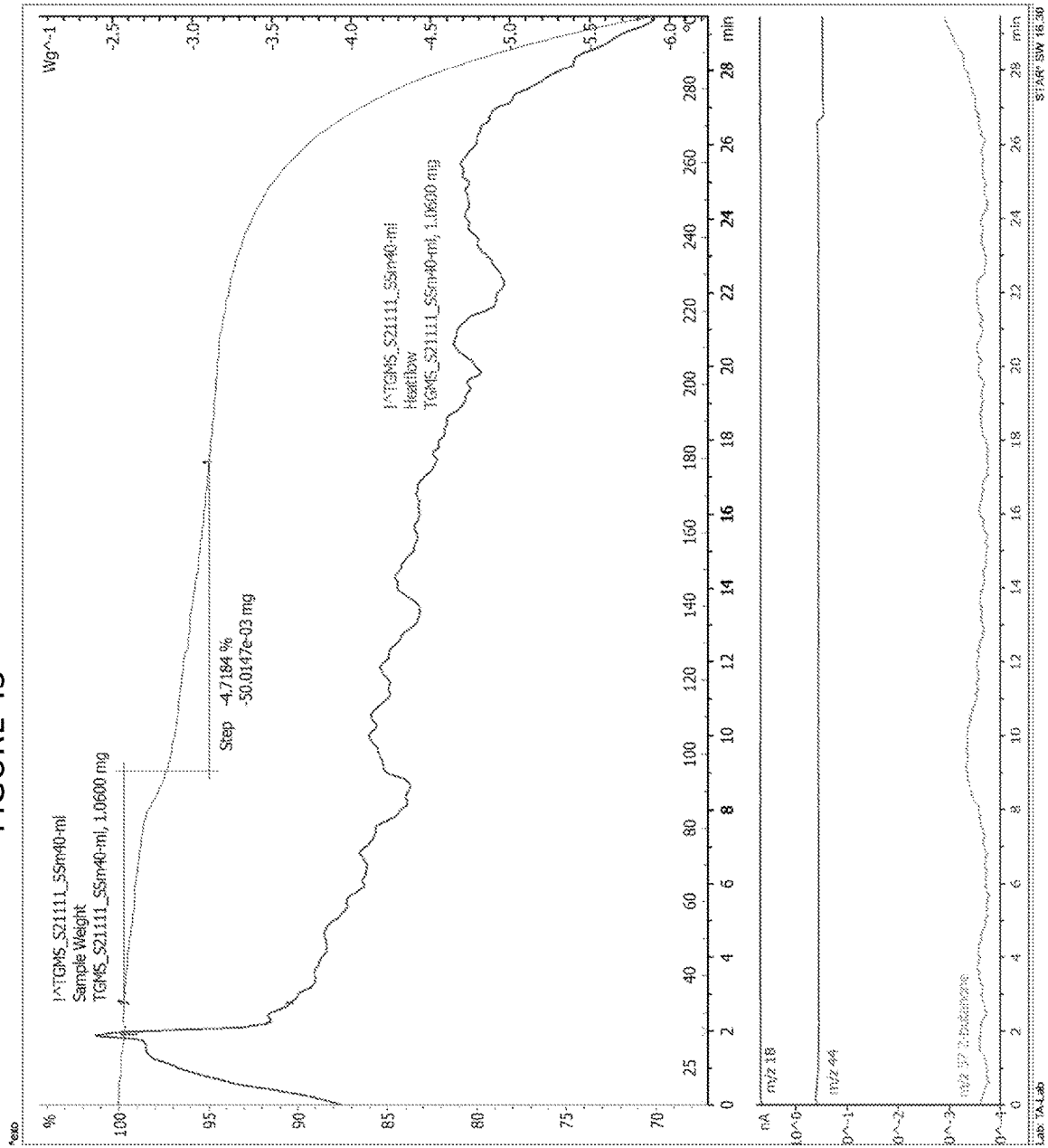
FIG. 43 is a TGMS analysis (heating rate of 10° C./min) of HBr1.
Figure 44:
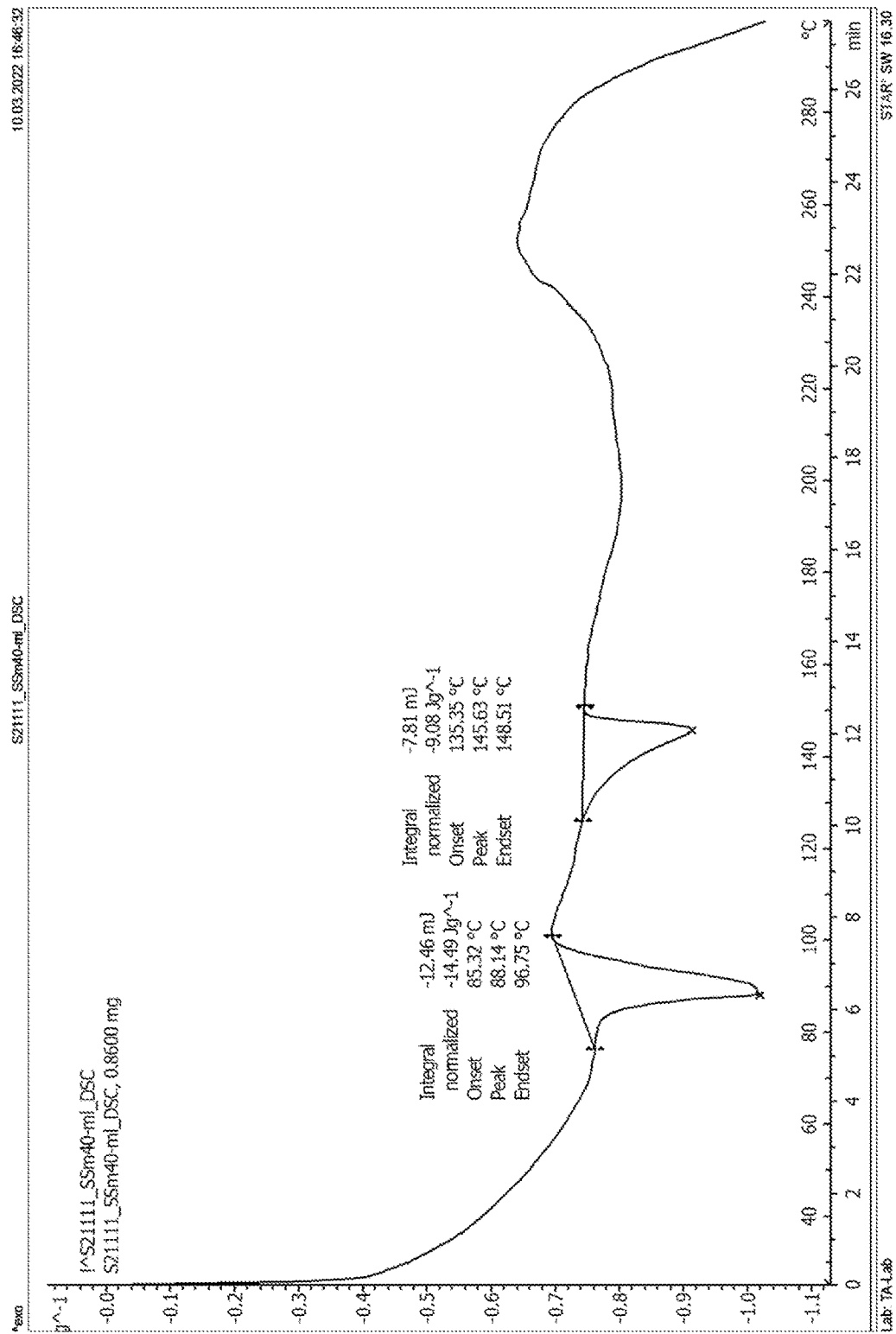
FIG. 44 is a DSC analysis (heating rate of 10° C./min) of HBr1.
Figure 45:
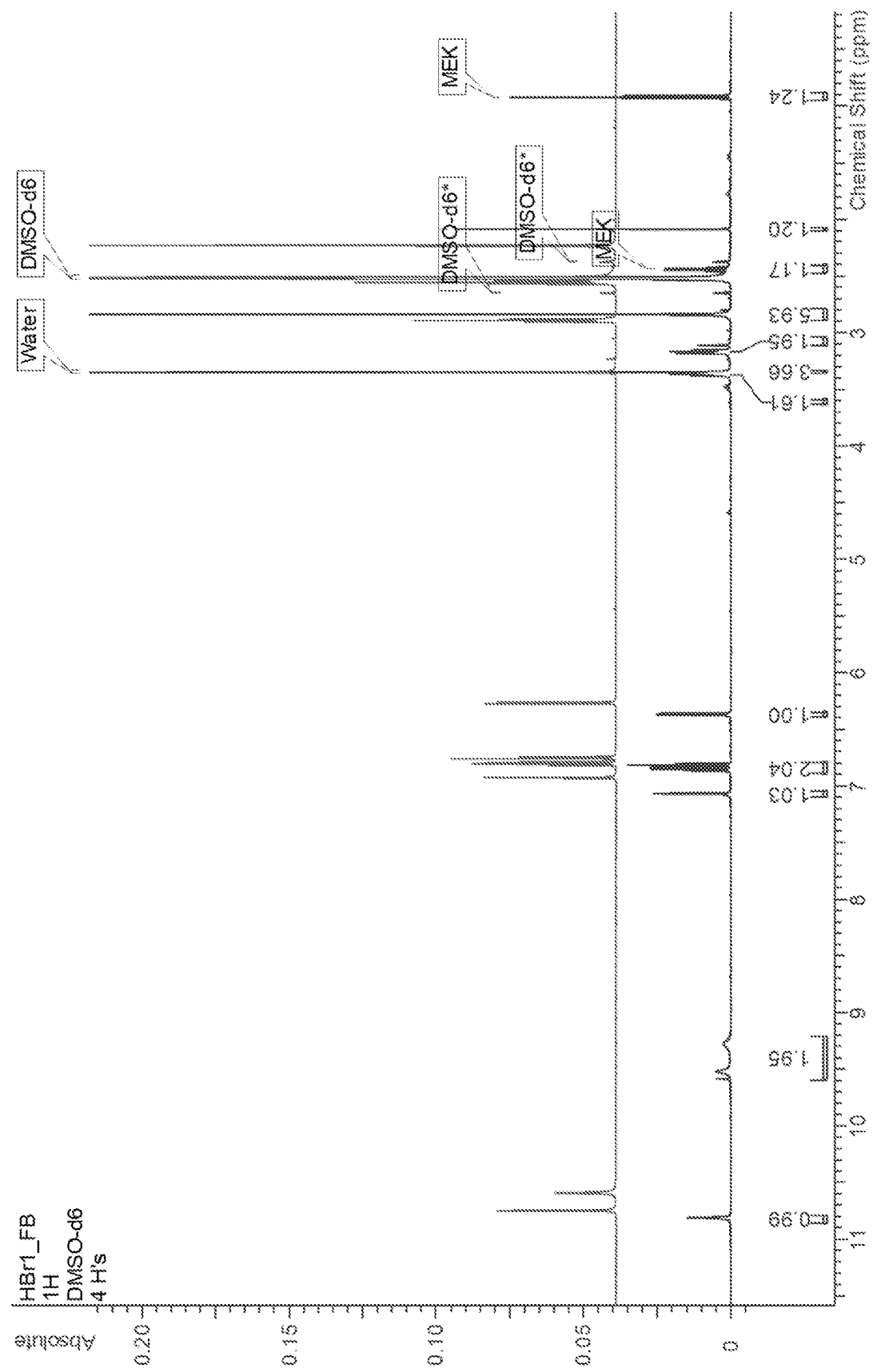
FIG. 45 is an overlay of $^1$H-NMR spectra (DMSO-d$_6$, 500 MHz) of HBr1 (bottom line), and the received batch of free base (top line).

The TGMS analysis of HBr1 (FIG. 43) showed a mass loss of 4.7% in the range 25-180° C., which could correspond to 0.20 MEK molecules per API salt unit. The DSC trace of HBr1 (FIG. 44) showed two endothermic events at 88.1° C. and at 145.6° C., possibly related to the mass loss observed by TGMS analysis and melting, respectively. The $^1$H-NMR spectrum of HBr1 is shown in FIG. 45. The API peaks shifted compared to the free base, confirming salt formation took place. Since hydrobromic acid is an inorganic counterion, the stoichiometry was not confirmed. About 0.4 molar equivalent of MEK were detected (or 9.2%).

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A composition of psilocin that is stable consisting of:
   a pharmaceutical salt of psilocin that provides enhanced stability wherein said salt is formed between psilocin and an anion chosen from the group consisting of besylate and lactate; and
   a pharmaceutically acceptable carrier, wherein enhanced stability includes being shelf-stable, being stable in cold storage, and being stable in storage under inert conditions.

2. The composition of claim 1, wherein enhanced stability includes being shelf-stable, being stable in cold storage, and being stable in storage under inert conditions, wherein said composition is in a formulation chosen from the group consisting of a liquid dosage form and a solid dosage form, and wherein said composition is in a formulation chosen from the group consisting of a liposome formulation and a nanoparticle formulation.

* * * * *